United States Patent [19]
Leung et al.

[11] Patent Number: 6,136,964
[45] Date of Patent: Oct. 24, 2000

[54] MAMMALIAN LYSOPHATIDIC ACID ACYLTRANSFERASE

[75] Inventors: David W. Leung, Mercer Island; James W. West, Seattle; Christopher K. Tompkins, Bothell, all of Wash.

[73] Assignee: Cell Therapeutics, Inc., Seattle, Wash.

[21] Appl. No.: 08/618,651

[22] Filed: Mar. 19, 1996

[51] Int. Cl.[7] .............................. C07H 21/04; C12N 9/10; C12N 9/12
[52] U.S. Cl. .......................... 536/23.2; 435/193; 435/194
[58] Field of Search ........................... 536/23.2; 435/194, 435/193

[56] References Cited

U.S. PATENT DOCUMENTS

| | | | |
|---|---|---|---|
| 5,563,058 | 10/1996 | Davies et al. | 435/193 |
| 5,652,243 | 7/1997 | Bianco et al. | 514/263 |

FOREIGN PATENT DOCUMENTS

| | | |
|---|---|---|
| RD400054A | 8/1997 | United Kingdom . |
| WO 95/27791 | 10/1995 | WIPO . |

OTHER PUBLICATIONS

Brough et al., *Molecular Breeding*, vol. 2, No. 2, p. 133–142, "Towards the genetic engineering of triacylglycerols of defined fatty acid composition: major changes in erucic acid content at the sn–2 position affected by the introduction of a 1–acyl–sn–glycerol–3–phosphate acyltransferase from *Limnanthes douglasii* into oil seed rape," 1996.

Coleman, *Mol. Gen. Genet.* vol. 232, p. 295–303, "Characterization of the *Escherichia coli* gene for 1–acyl–sn–glycerol–3–phosphate acyltransferase (plsC)," 1992.

Eberhardt et al., *J. Biol. Chem.* vol. 272, No. 32, p. 20299–20305, "Human Lysophosphatidic Acid Acyltransferase," 1997.

Kamisaka et al., *J. Biochem.*, vol. 121, No. 6, p. 1107–1114, "Purification and Characterization of Diacylglycerol Acyltransferase from the Lipid Body Fraction of an Oleaginous Fungus," 1997.

Knutzon et al., *Plant Phys.*, vol. 109, p. 999–1006, "Cloning of a Coconut Endosperm cDNA Encoding a 1–Acyl–sn–Glycerol–3–Phosphate Acyltransferase that Accepts Medium–Chain–Length Substrates," 1995.

Stamps et al., *Biochem. J.*, vol. 326, p. 455–461, "A human cDNA sequence with homology to non–mammalian lysophosphatidic acid acyltransferases," 1997.

International Search Report Nov. 19, 1997.

Brown et. al., *Plant Molecular Biology*, vol. 26: 211–223 (1994), "Isolation and characterization of a maize cDNA that complements a 1–acyl sn–glyerol–3–phosphate acyltransferase mutant of *Escherichia coli* and encodes a protein which has similarities to other acyltransferases".

Brown et al., *Plant Molecular Biology*, vol. 29: 267–278 (1995), "Identification of a cDNA that encodes a 1–acyl–sn–glycerol–3–phosphate acyltransferase from *Limnanthes douglasii*".

Coleman, *Mol Gen Genet,* vol. 232: 295–303 (1992), "Characterization of the *Escherichia coli* gene for 1–acyl–sn–glycerol–3–phosphate acyltransferase (plsC)".

Hanke et al., *Eur. J. Biochem*, vol. 232: 806–810 (1995), "A plant acyltransferase involved in triacylglycerol biosynthesis complements as *Escherichia coli* sn–1–acylglycerol–3–phosphate acyltransferase mutant".

Knutzon et al., *Plant Physiol,* vol. 109: 999–1006 (1995), "Cloning of a Coconut Endosperm cDNA Encoding a 1–Acyl–sn–Glycerol–3–Phosphate Acyltransferase That Accepts Medium–Chain–Length Substrates".

Lassner et al., *Plant Physiol.,* vol. 109: 1389–1394 (1995), "Lysophosphatidic Acid Acyltransferase from Meadowfoam Mediates Insertion of Erucic Acid at the sn–2 Position of Triacylglycerol in Transgenic Rapeseed Oil".

Nagiec et al., *The Journal of Biological Chemistry*, vol. 268(29): 22156–22163 (1993), "A Suppressor Gene That Enables *Saccharomyces cerevisiae* to Grow without Making Sphingolipids Encodes a Protein That Resembles an *Escherichia coli* Fatty Acyltransferase".

Swartley et al., *Molecular Microbiology*, vol. 18(3): 401–412 (1995), "Membrane glycerophospholipid biosynthesis in *Neisseria meningitidis* and *Neisseria gonorrhoeae:* identification, characterization and mutagenesis of a lysophosphatidic acid acyltransferase".

Sigma Catalog 1995, Sigma Chemical Company, St. Louis, Missouri. Pp. 320, 322, 323 and 327, Jan. 1995.

Primary Examiner—Bradley Sisson
Assistant Examiner—Einar Stole
Attorney, Agent, or Firm—Stephen Faciszewski; Susan J. Friedman

[57] ABSTRACT

There is disclosed cDNA sequences and polypeptides having the enzyme lysophosphatidic acid acyltransferase (LPAAT) activity. LPAAT is also known as 1-acyl sn-glycerol-3-phosphate acyltransferase.

3 Claims, 25 Drawing Sheets

Figure 1

```
  1 GGAAGTCAGCAGGCCGTTGGGGAGGTGGGGGAATAGCGGGGCAGC
 51 AGCCCCAGCCCTCAGAGACAGCAGAAAGGGAGGGAGGGAGGGTGCTGG
101 GGGGACAGCCCCCACCATTCCCTACCGCTATGGCCCAACCTCCCACTCC
151 CACCTCCCCCTCCATCGGCCCGGGCTAGGACACCCCCAAATCCCGTCGCCC
201 CCTTGGCACCACCCCGACACCCGACAGAGACACAGCCATCCGCCACCA
251 CCGCTGCCGCAGCCTGGCTGGGGCCCCCCAGCCCCAGCCCCCTAC
301 CCCTCTGAGGTGGCCAGA ATG GAT TTG TGG CCA GGG GCA TGG
                       Met Asp Leu Trp Pro Gly Ala Trp
343 ATG CTG CTG CTG CTC TTC CTG CTG CTG CTC TTC C
    Met Leu Leu Leu Leu Phe Leu Leu Leu Leu Phe L
                           10                    20
380 TG CTG CCC ACC CTG TGG TTC TGC AGC CCC AGT GCC AAG
    eu Leu Pro Thr Leu Trp Phe Cys Ser Pro Ser Ala Lys
                                                   30
```

Figure 1 (continued)

```
418  TAC TTC TTC AAG ATG GCC TTC TAC AAT GGC TGG ATC C
     Tyr Phe Phe Lys Met Ala Phe Tyr Asn Gly Trp Ile L
                      40

455  TC TTC CTG GCT GTG CTC GCC ATC CCT GTG TGT GCC GTG
     eu Phe Leu Ala Val Leu Ala Ile Pro Val Cys Ala Val
                      50

493  CGA GGA CGC AAC GTC GAG AAC ATG AAG ATC TTG CGT C
     Arg Gly Arg Asn Val Glu Asn Met Lys Ile Leu Arg L
                      60                            70

530  TA ATG CTG CTC CAC ATC AAA TAC CTG TAC GGG ATC CGA
     eu Met Leu Leu His Ile Lys Tyr Leu Tyr Gly Ile Arg
                                  80
```

Figure 1 (continued)

```
568  GTG GAG GTG CGA GGG GCT CAC CAC TTC CCT CCC TCG C
     Val Glu Val Arg Gly Ala His His Phe Pro Pro Ser G
                          90

605  AG CCC TAT GTT GTT GTC TCC AAC CAC CAG AGC TCT CTC
     ln Pro Tyr Val Val Val Ser Asn His Gln Ser Ser Leu
                          100

643  GAT CTG CTT GGG ATG ATG GAG GTA CTG CCA GGC CGC T
     Asp Leu Leu Gly Met Met Glu Val Leu Pro Gly Arg C
                          110                      120

680  GT GTG CCC ATT GCC AAG CGC GAG CTA CTG TGG GCT GGC
     ys Val Pro Ile Ala Lys Arg Glu Leu Leu Trp Ala Gly
                                                   130
```

Figure 1 (continued)

718 TCT GCC GGG CTG GCC TGC TGG CTG GCA GGA GTC ATC T
    Ser Ala Gly Leu Ala Cys Trp Leu Ala Gly Val Ile P
                            140

755 TC ATC GAC CGG AAG CGC ACG GGG GAT GCC ATC AGT GTC
    he Ile Asp Arg Lys Arg Thr Gly Asp Ala Ile Ser Val
                            150

793 ATG TCT GAG GTC GCC CAG ACC CTG CTC ACC CAG GAC G
    Met Ser Glu Val Ala Gln Thr Leu Leu Thr Gln Asp V
                    160                    170

830 TG AGG GTC TGG GTG TTT CCT GAG GGA ACG AGA AAC CAC
    al Arg Val Trp Val Phe Pro Glu Gly Thr Arg Asn His
                                    180

Figure 1 (continued)

868 AAT GGC TCC ATG CTG CCC TTC AAA CGT GGC GCC TTC C
    Asn Gly Ser Met Leu Pro Phe Lys Arg Gly Ala Phe H
                                190

905 AT CTT GCA GTG CAG GCC CAG GTT CCC ATT GTC CCC ATA
    is Leu Ala Val Gln Ala Gln Val Pro Ile Val Pro Ile
                                200

943 GTC ATG TCC TCC TAC CAA GAC TTC TAC TGC AAG AAG G
    Val Met Ser Ser Tyr Gln Asp Phe Tyr Cys Lys Lys G
                                210                    220

980 AG CGT CGC TTC ACC TCG GGA CAA TGT CAG GTG CGG GTG
    lu Arg Arg Phe Thr Ser Gly Gln Cys Gln Val Arg Val
                                                230

Figure 1 (continued)

```
1018 CTG CCC CCA GTG CCC ACG GAA GGG CTG ACA CCA GAT G
     Leu Pro Pro Val Pro Thr Glu Gly Leu Thr Pro Asp A
                                240

1055 AC GTC CCA GCT CTG GCT GAC AGA GTC CGG CAC TCC ATG
     sp Val Pro Ala Leu Ala Asp Arg Val Arg His Ser Met
                                  250

1093 CTC ACT GTT TTC CGG GAA ATC TCC ACT GAT GGC CGG G
     Leu Thr Val Phe Arg Glu Ile Ser Thr Asp Gly Arg G
                    260

1130 GT GGT GGT GAC TAT CTG AAG AAG CCT GGG GGC GGT GGG
     ly Gly Gly Asp Tyr Leu Lys Lys Pro Gly Gly Gly Gly 280
                                                    270

1168 TGA ACCCTGGCTCTGAGCTCTCCTCCCCATCTGTCCCCATCTTCCTCCC

1216 CACACCTTACCCACCCAGTGGGCCCTGAAGCAGGGCCAAACCCTCTTCCTT

1266 GTCTCCCCTCCTCCCCACTTATTCTCTCTTTGGAATCTTCAACTTCTGAA
```

Figure 1 (continued)

```
1316 GTGAATGTGGATACAGGCCACTCCTGCCCCCTCTTGGCCCCATCCATGG
1366 ACTCTTGCCTCGGTGCAGTTTCCACTCTTGACCCCACCTCCTACTGTCT
1416 TGTCTGTGGGACAGTTGCCCTCCATCTCCAGTGACTCAGCCTACAC
1466 AAGGAGGGGAACATTCCATCCCCAGTGGAGTCTCTTCCTATGTGGTCTT
1516 CTCTACCCCTCTACCCCCACATTGGCCAGTGGACTCATCCATTCTTTGGA
1566 ACAAATCCCCCCCACTCCAAAGTCCATGGATTCAATGGACTCATCCATT
1616 TGTGAGGAGGACTTCTCGCCCTCTGGCTGGAAGCTGATACCTGAAGCACT
1666 CCCAGGCTCATCCTGTCAGTGGGCTGGACCCTTCACTTCCCTCCCCAG
1716 TGTAGCCTGCCCAGATGCCCAGGGTCGTGCACTCTCTGGATACCAGT
1766 GCCTGCCCTTGCCCACCCAGCCCTGCTGACCCTGTTTCTGTCCCCATAGTACAGTTCTTCAGTG
1816 TCAGTCTCCACATTTCTGGTTTTCTGTCCCCATAGTACAGTTCTTCAGTG
1866 GACATGACCCCACCCAGCCCTGCTGACCATCTCACCAGAC
1916 ACAAGGGGAAGAAGCAGACATCAGGTGCTGCACTCACTTCTGCCCCTGG
1966 GGAGTTGGGGAAAGGAACGAACCCTGGCTGGAGGGGATAGGAGGGCTTTT
```

Figure 1 (continued)

2016 AATTTATTTCTTTTTCTGTTGAGGCTTCCCCTCTCTGAGCCCAGTTTTCA
2066 TTTCTTCCTGGTGGCATTAGCCACTCCCTGCCTCTCACTCCAGACCCTGTT
2116 CCCACAACTGGGGAGGTAGGCTGGGAGCAAAGGAGAGAGGGTGGGACCCAG
2166 TTTGCGTGGTTGGTTTTTATTAATTATCTGGATAACAGCAAAAAACTG
2216 AAAATAAAGAGAGAGAGAAAAAAAAA

Figure 2

```
                  10         20         30         40         50
Human LPAAT    1  MDLWPGAWM- ----LLLLLF LL-LLFLLPT LWFCSPSAKY F----FKMA
Yeast LPAAT    1  MSV-IGRFLY YLRSVL-VVL AL-AG----- ---C------ --------G
E.coli LPAAT   1  M--------- ---------- --LYIF RL-IITVIYS ILVCVFGSIY ----------
Maize LPAAT    1  MAI------- ---PLVLVVL PLGLLFLLSG LIVNAIQAVL FVTIRPFSKS 60         70         80         90         100
Human LPAAT   51  FYNGWILFLA VLAIPVCAVR GRNVENMKIL RLMLLHIKYL -YGIRVEVRG
Yeast LPAAT   51  FY-------G ---------- VIASILCTLI GKQHLAQWIT ARCFYHVMKL MLGLDV---K
E.coli LPAAT  51  ---------- ---------- ----CLFS   PRNPKHVATF GHMFGRLAPL -FGLKVECRK
Maize LPAAT   51  FYRRINRFLA EL-------- ---------L WLQLVWVVDW WAGVKVQLHA 110        120        130        140        150
Human LPAAT  101  AHHF-PPSQ- -PYVVVSNHQ SSLDLLGMME VL---PGRC- -VPI-AKREL
Yeast LPAAT  101  VVGE-ENLAK KPYIMIANHQ STLDIFMLGR IF---PPGCT- ---VTAKKSL
E.coli LPAAT 101  PTDA-ESYG- -NAIYIANHQ NNYDMVTASN IVQ--PP--- TVTV-GKKSL
Maize LPAAT  101  DEETYRSMGK EHALIISNHR SDIDWL-IGW ILAQRSGCLG STLAVMKKSS 160        170        180        190        200
Human LPAAT  151  LWAGSAGLAC W---LAGVIF IDRKRTGDAI SVMSEVAQTL LTQDVRVWV-
Yeast LPAAT  151  KYVPFLG--- WFMALSGTYF LDRSKRQEAI DTLNKGLENV KKNKRALWV-
E.coli LPAAT 151  LWIPFFGQLY W---LTGNLL IDRNNRTKAH GTIAEVVNHF KKRRISIWM-
Maize LPAAT  151  KFLPVIGWSM WF---AEYLF LERS-WAKDE KTLKWGLQRL KDFPRPFWLA 210        220        230        240        250
Human LPAAT  201  -FPEGTRNHN GS-------- ---------- MLPFKRGAFH LAVQAQVPIV
Yeast LPAAT  201  -FPEGTRSYT SEL------- ---------- MLPFKKGAFH LAQQGKIPIV
E.coli LPAAT 201  -FPEGTRSRG RGL------- --------T- -LPFKTGAFH AAIAAGVPII
Maize LPAAT  201  LFVEGTRFTP AKLLAAQEYA ASQGLPAPRN VLIPRTKGFV SAVSIMRDFV
```

Figure 2 (continued)

```
                  260        270        280        290        300
Human LPAAT  251  PIVMSSYQDF YCKKERRFTS GQCQVRVLPP VPTEGLTPDD VPALADR---
Yeast LPAAT  251  PVVVSNTSTL VSPKYGVFNR GCMIVRILKP ISTENLTKDK IGEFAEK---
E.coli LPAAT 251  PVCVSTTSNK I--NLNRLHN GLVIVEMLPP IDVSQYGKDQ VRELAAH---
Maize LPAAT  251  PAIYDTT--V IVPKDSPQPT MLRILKGQSS VIHVRMKRHA MSEMPKSDED 310        320        330        340        350
Human LPAAT  301  ---------- VRHSMLTV-F REISTDGRGG GDYLKKPGGG G*........
Yeast LPAAT  301  ---------- VRDQMVDT-L KEIGYSPAIN DTTLPPQ--- ..........
E.coli LPAAT 301  ---------- CRSIMEQK-I AELDKEVAE- ----REAAGK V*........
Maize LPAAT  301  VSKWCKDIFV AKDALLDKHL ATGTFDEEIR PIGRPVKSLL VTLFWSCLLL 360        370        380        390        400
Human LPAAT  351  .......... --AIEY---A AL------Q HDKKVNKKIK NEPVPSVSIS
Yeast LPAAT  351  .......... .......... .......... .......... ..........
E.coli LPAAT 351  .......... .......... .......... .......... ..........
Maize LPAAT  351  FGAIEFFKWT QLLSTWRGVA FTAAGMALVT GVMHVFIMFS QA------ERS 410        420        430        440        450
Human LPAAT  401  .......... .......... .......... .......... ..........
Yeast LPAAT  401  S-------V KKMH*..... .......... .......... ..........
E.coli LPAAT 401  .......... .......... .......... .......... ..........
Maize LPAAT  401  SSARAARNRV KKE*...... .......... .......... ..........
```

Figure 3

```
          10         20         30         40         50         60
GGAGCCAGCT GGCGGGCGCCG TCGGGGCGCCG GGCCGGGCCA TGGAGCTGTG GCCGTGTCTG 70         80         90        100        110        120
GCCGCGGCGC TGCTGTTGCT GCTGCTGCTG GTGCAGCTGA GCCGCGCGGC CGAGTTCTAC 130        140        150        160        170        180
GCCAAGGTCG CCCTGTACTG CGCGCTGTGC TTCACGGTGT CCGCCCGTGGC CTCGCTCGTC 190        200        210        220        230        240
TGCCTGCTGT GCCACGGCGG CCGGACGGTG GAGAACATGA GCATCATCGG CTGGTTCGTG 250        260        270        280        290        300
CGAAGCTTCA AGTACTTTTA CGGGCTCCCGC TTCGAGGTGC GGGACCCCGCG CAGGCTGCAG 310        320        330        340        350        360
GAGGCCCGTC CCTGTGTCAT CGTCTCCAAC CACCAGAGCA TCCTGGACAT GATGGGCCTC 370        380        390        400        410        420
ATGGAGGTCC TTCCCGGAGCG CTGCCGTGCAG ATCGCCAAGC GGGAGCTGCT CTTCCTGGGG 430        440        450        460        470        480
CCCGTGGGCC TCATCATGTA CCTCGGGGGC GTCTTCTTCA TCAACCGGCA GCGCTCTAGC 490        500        510        520        530        540
ACTGCCATGA CAGTGATGGC CGACCTGGGC GAGGCGCATGG TCAGGGAGAA CCTCAAAGTG
```

Figure 3 (continued)

```
550        560        570        580        590        600
TGGATCTATC CCGAGGGTAC TCGCAACGAC AATGGGGACC TGCTGCCTTT TAAGAAGGGC
610        620        630        640        650        660
GCCTTCTACC TGGCAGTCCA GGCACAGGTG CCCATCGTCC CCGTGGTGTA CTCTTCCTTC
670        680        690        700        710        720
TCCTCCTTCT ACAACACCAA GAAGAAGTTC TTCACTTCAG GAACAGTCAC AGTGCAGGTG
730        740        750        760        770        780
CTGGAAGCCA TCCCCACCAG CGGCCTCACT GCGGCGGACG TCCCTGCGCT CGTGGACACC
790        800        810        820        830        840
TGCCACCGGG CCATGAGGAC CACCTTCCTC CACATCTCCA AGACCCCCCA GGAGAACGGG
850        860        870        880        890        900
GCCACTGCGG GGTCTGGCGT GCAGCCGGCC CAGTAGCCCA GACCACGGCA GGGCATGACC
910        920        930        940        950        960
TGGGGAGGGC AGGTGGAAGC CGATGGCTGG AGGATGGGCA GAGGGACTC CTCCCGGCTT
970        980        990        1000       1010       1020
CCAAATACCA CTCTGTCCGG CTCCCCCAGC TCTCACTCAG CCCGGGAAGC AGGAAGCCCC
1030       1040       1050       1060       1070       1080
TTCTGTCACT GGTCTCAGAC ACAGGCCCCT GGTGTCCCCT GCAGGGGGCT CAGCTGGACC
```

Figure 3 (continued)

```
           1090       1100       1110       1120       1130       1140
      CTCCCCGGGC TCGAGGGCAG GGACTCGCGC CCACGGCACC TCTGGGNGCT GGGNTGATAA
           1150       1160       1170       1180       1190       1200
      AGATGAGGCT TGCGGCTGTG GCCCGCTGGT GGGCTGAGCC ACAAGGCCCC CGATGGCCCA
           1210       1220       1230       1240       1250       1260
      GGAGCAGATG GGAGGACCCC GAGGCCAGGA GTCCCAGACT CACGCACCCT GGGCCACAGG
           1270       1280       1290       1300       1310       1320
      GAGCCGGGAA TCGGGGCCTG CTGCTCCCTG TGGCCTGAAG AATCTGTGGG GTCAGCACTG
           1330       1340       1350       1360       1370       1380
      TACTCCGTTG CTGTTTTTTT ATAAACACAC TCTTGGAAAA AAAAAAAAAA AAAAAAAAAA
           1390       1400       1410       1420       1430       1440
      AAA.:..... .......... .......... .......... .......... ..........
```

Figure 4

```
        10         20         30         40         50
GGAGCGAGCTGGCCGCGCCCGTCGGGCCGCGGGCC ATG GAG CTG TGG CCG
                                    Met Glu Leu Trp Pro 60         70         80         90
TGT CTG GCC GCG GCG CTG CTT CTG CTG CTG CTG GTG CAG CTG
Cys Leu Ala Ala Ala Leu Leu Leu Leu Leu Leu Val Gln Leu
                    10                              20

100        110        120        130        140
AGC CGC GCG GCC GAG TTC TAC GCC AAG GTC GCC CTG TAC TGC GCG
Ser Arg Ala Ala Glu Phe Tyr Ala Lys Val Ala Leu Tyr Cys Ala
                                        30

150        160        170        180
CTG TGC TTC ACG GTG TCC GCC GTG GCC TCG CTC GTC TGC CTG CTG
Leu Cys Phe Thr Val Ser Ala Val Ala Ser Leu Val Cys Leu Leu
                40                                      50

190        200        210        220        230
TGC CAC GGC GGC CGG ACG GTG GAG AAC ATG AGC ATC ATC GGC TGG
Cys His Gly Gly Arg Thr Val Glu Asn Met Ser Ile Ile Gly Trp
                                        60
```

Figure 4 (continued)

```
     240         250         260         270
TTC GTG CGA AGC TTC AAG TAC TTT TAC GGG CTC CGC TTC GAG GTG
Phe Val Arg Ser Phe Lys Tyr Phe Tyr Gly Leu Arg Phe Glu Val
                     70                                  80

280         290         300         310         320
CGG GAC CCG CGC AGG CTG CAG GAG GCC CGT CCC TGT GTC ATC GTC
Arg Asp Pro Arg Arg Leu Gln Glu Ala Arg Pro Cys Val Ile Val
                                 90

330         340         350         360
TCC AAC CAC CAG AGC ATC CTG GAC ATG ATG GGC CTC ATG GAG GTC
Ser Asn His Gln Ser Ile Leu Asp Met Met Gly Leu Met Glu Val
                100                                 110

370         380         390         400         410
CTT CCG GAG CGC TGC GTG CAG ATC GCC AAG CGG GAG CTG CTC TTC
Leu Pro Glu Arg Cys Val Gln Ile Ala Lys Arg Glu Leu Leu Phe
                                120

420         430         440         450
CTG GGG CCC GTG GGC CTC ATC ATG TAC CTC GGG GTC TTC TTC
Leu Gly Pro Val Gly Leu Ile Met Tyr Leu Gly Val Phe Phe
                130                                 140

460         470         480         490         500
ATC AAC CGG CAG CGC TCT AGC ACT GCC ATG ACA GTG ATG GCC GAC
Ile Asn Arg Gln Arg Ser Ser Thr Ala Met Thr Val Met Ala Asp
                                150
```

Figure 4 (continued)

```
      510             520             530             540
CTG GGC GAG CGC ATG GTC AGG GAG AAC CTC AAA GTG TGG ATC TAT
Leu Gly Glu Arg Met Val Arg Glu Asn Leu Lys Val Trp Ile Tyr
                         160                             170

550             560             570             580             590
CCC GAG GGT ACT CGC AAC GAC AAT GGG GAC CTG CTG CCT TTT AAG
Pro Glu Gly Thr Arg Asn Asp Asn Gly Asp Leu Leu Pro Phe Lys
                                         180

600             610             620             630
AAG GGC GCC TTC TAC CTG GCA GTC CAG GCA CAG GTG CCC ATC GTC
Lys Gly Ala Phe Tyr Leu Ala Val Gln Ala Gln Val Pro Ile Val
                         190                             200

640             650             660             670             680
CCC GTG GTG TAC TCT TCC TCC TTC TAC AAC ACC AAG AAG
Pro Val Val Tyr Ser Ser Ser Phe Tyr Asn Thr Lys Lys
                                         210

690             700             710             720
AAG TTC ACT TCA GGA ACA GTC ACA GTG CAG GTG CTG GAA GCC
Lys Phe Thr Ser Gly Thr Val Thr Val Gln Val Leu Glu Ala
                         220                             230
```

Figure 4 (continued)

```
730        740        750        760        770
ATC CCC ACC AGC GGC CTC ACT GCG GCG GAC GTC CCT GCG CTC GTG
Ile Pro Thr Ser Gly Leu Thr Ala Ala Asp Val Pro Ala Leu Val
                                240

780        790        800        810
GAC ACC TGC CAC CGG GCC ATG AGG ACC ACC TTC CTC CAC ATC TCC
Asp Thr Cys His Arg Ala Met Arg Thr Thr Phe Leu His Ile Ser
                    250                                 260

820        830        840        850        860
AAG ACC CCC CAG GAG AAC GGG GCC ACT GCG GGG TCT GGC GTG CAG
Lys Thr Pro Gln Glu Asn Gly Ala Thr Ala Gly Ser Gly Val Gln
                                            270

870        880        890        900        910        920
CCG GCC CAG TAG CCCAGACCACGGGCAGGGCATGACCTGGGGAGGCAGGTGGAAGC
Pro Ala Gln ***

940        950        960        970        980
CGATGGCTGGAGGATGGGCAGAGGGACTCCTCCCGGCTTCCAAATACCACTCTGTCCGG 1000       1010       1020       1030       1040
CTCCCCCAGCTCTCACTCAGCCCGGAAGCAGGAAGCCCCTTCTGTCTGTCACTGGTCTCAGAC
      1050       1060       1070       1080       1090       1100
ACAGGCCCCCTGTGTCCCCTGCAGGGGGCTCAGCTGCAGCTGGACCCTCCCCCGGGCTCGAGGGCAG

```
            1130        1140        1150        1160
1110 1120 GGACTCGCGCCACGGCCCACCTCTGGGNGCTGGGNTGATAAAGATGAGGCTTGCGGCTGTG 1190        1200        1210        1220
1170 1180 GCCCGCTGGTGGGCTGAGCCACAAGGCCCCCGATGGCCCAGGAGCAGATGGGAGGACCCC 1250        1260        1270        1280
1230 1240 GAGGCCAGGAGTCCCAGACTCACGCACCCTGGCCACAGGAGCCGGGAATCGGGGCCTG 1310        1320        1330        1340
1290 1300 CTGCTCCTGCTGGCCTGAAGAATCTGTGGGGTCAGCACTGTACTCCGTTGCTGTTTTTT 1370        1380
1350 1360 ATAAACACACTCTTGGAAAAAAAAAAAAAAAAAAAA
```

Figure 5

Alignment of LPAAT Sequences.

```
                       10         20         30         40         50
Human LPAAT-β   1  ------------------------------MEL WPC------LA AAILLLLLV
Human LPAAT-α   1  ----------------------------- MDL WPGAWMLLL LFLLILFLLP
Yeast LPAAT     1  ---------------------------- MSV --IGRFLYYL RSVLWLALA
E.coli LPAAT    1  --------------------------------------------------
H.influenzae    1  --------------------------------------------------
S.typhimuriu    1  --------------------------------------------------
L.douglassi     1  MAKIRTSS-L RNR---------- ---------RQKP AVAATAD--D DKDGVFM--
C. nucifera     1  MDASGASSFL RGRCLESCFK ASFGMSQPKD AAGQPSRRPA DADDFFIVDD 60         70         80         90        100
Human LPAAT-β  51  QL--SRAAE FYAKVAL-YC ALCFTVSAVA SIVCLLCHGG RTVENM-SII
Human LPAAT-α  51  TLWFCSPSAK YFFKMAF-YN GWIFLAVLA IPVCAV--RG RNVENM-KIL
Yeast LPAAT    51  G------FY--------- -------GVIA SLICTLIGKQ HLAQWI-TAR
E.coli LPAAT   51  ----MLYI FRLITVIYS ILVC---VFG SIYCLESPRN PKHV--ATF
H.influenzae   51  ----MLKL LRIFLMLICC ILIC----VLG TIYSFIRFKN PSNV---GIV
S.typhimuriu   51  ----MLYI FRLIVTIYS ILVC---VFG SIYCLESPRN PKHV--ATF
L.douglassi    51  ----LLSC FKIFVCFAFT VVLITAVAWG LIMLLLPWP YMRIRIGNLY
C. nucifera    51  DRWITVILSV VRIAACFL-- SMMTTLVWN MIMILLPWP YARIRQGNLY
```

Human LPAAT-β
Human LPAAT-α
Yeast LPAAT
E.coli LPAAT
H.influenzae
S.typhimuriu
L.douglassi
C. nucifera

Figure 5 (continued)

```
                    110        120        130        140        150
Human LPAAT-β   101 GWFVRSFKY- ---------  ---------- ---------- ----------
Human LPAAT-α   101 RLMLHIKY-- ---------- ---------- ---------- ----------
Yeast LPAAT     101 CFY-HVMKL- ---------- ---------- ---------- ----------
E.coli LPAAT    101 GHMFGRL--- ---------- ---------- ---------- ----------
H.influenzae    101 ARWFGRL-FT ---------- ---------- ---------- ----------
S.typhimuriu    101 GHMFGRL-FT ---------- ---------- ---------- ----------
L.douglassi     101 GHIIGLV--- ---------- ---------- ---------- ----------
C. nucifera     101 GHVIGRMLFT ---------- ---------- ---------- ----------

110        120        130        140        150
Human LPAAT-β   101 GWFVRSFKY- --FYGLRFEV RDPRRLQEAR PCVIVSNHQS ILDMMGIMEV
Human LPAAT-α   101 RLMLHIKY-- ---LYGIRVEV RGAHHFPPSQ PYVVVSNHQS SLDILGVMEV
Yeast LPAAT     101 CFY-HVMKL- --MLGLDVKV VGEENAK-K PYIMANHQS TLDIFMGRI
E.coli LPAAT    101 GHMFGRL--- APLFGLKVEC RKPIDAESYG NAIYIANHQN NYDMVTASNI
H.influenzae    101 ARWFGRL-FT YPLFGLKVEH RIPQDKQIS RAIYIGNHQN NYDMVT ISM
S.typhimuriu    101 GHMFGRL-FT APLFGLKVEC RKPADAENYG NAIYIANHQN NYDMVTAANI
L.douglassi     101 GHIIGLV--- IWIYGIPIKI QGSEHIKKRA IFTYISNHAS PIDAFFVML
C. nucifera     101 GHVIGRMLFT MWILGNPITI EGSEFSNTRA I---YIONHAS LVDIFIIMWL 160        170        180        190        200
Human LPAAT-β   151 LPERCVQIAK RELLFLGPV- --GLIMYLGGV FFINRORSST AMT--VMAL
Human LPAAT-α   151 LPGRCVPIAK RELLIWAGSA- --GLACWLAGV IFIDKRIGD AIS--VMSEV
Yeast LPAAT     151 FPPGCIVTAK KSLKVVPFL- --GWFMALSGT YFLDRSKRQE AID--TINKG
E.coli LPAAT    151 VQPPTIVTGK KSLLWIPFF- --GQLYWLTGN LLIDRNNRIK AHG--TIAEV
H.influenzae    151 VQPRTVSVGK KSLLWIPFF F TGILLYWVIGN IFIDRENRTK AHN--TMSQL
S.typhimuriu    151 VQPPTIVTGK KSLLWIPFF F TGQLYWLTGN LLIDRNNRAK AHS--TIAAV
L.douglassi     151 APIGTVGVAK KEVIWYPLLG Q--LYTAHH IRIDRSNPAA AIQSFIMKEA
C. nucifera     151 IPKGTVTIAK KEIIWYPLFG QFTLYVLANH QRIDRSNPSA AIES--IKEV
```

Human LPAAT-β
Human LPAAT-α
Yeast LPAAT
E.coli LPAAT
H.influenzae
S.typhimuriu
L.douglassi
C. nucifera

Figure 5 (continued)

```
                    210        220         230        240          250
Human LPAAT-β   201 GERMRENLK  VWIYPEGTRN  DNGDL--LPF KKGAFYL--A   VQAQVPIVPV
Human LPAAT-α   201 AQILLQDVR  VWVFPEGTRN  HNGSM--LPF KRGAFHL--A   VQAQVPIVPI
Yeast LPAAT     201 LENVKNKRA  LWVFPEGTRS  YTSELMLPF  KKGAFHL--A   QQKIPIVPV
E.coli LPAAT    201 VNHFKKRRIS IWMFPEGTRS  RGRGL--LPF KIGAF--HAA   IAAGVPIIPV
H.influenzae    201 ARRINDNLS  IWMFPEGTRN  RGRGL--LPF KIGAFTFHAA   ISAGVPIIPV
S.typhimuriu    201 VNHFKKRRIS IWMFPEGTRS  RGRGL--LPF KIGAFTFHAA   IAAGVPIIPV
L.douglassi     201 VRVIEKNLS  LMFPEGTRS   GDGRL--LPF KKGFVHL--A   LQSHLPIVPM
C. nucifera     201 ARAWKNLS   LIIFPEGTRS  KIGRL--LPF KKGFIHFTIA   LQIRLPIVPM 260         270        280         290          300
Human LPAAT-β   251 VYSSFSS--F  YNIKKFFTS  GIVIVQVLEA  IPTSGLTAAD  VPALVDICR-
Human LPAAT-α   251 VMSSYQD--F  YCKKERFTS  GQQVRVLPP   VPTEGLTPDD  VPALADRVRH
Yeast LPAAT     251 VVSNIST--L  VSPKYGVFNR GMIVRILKP   ISTENLTKDK  IGEFAEKVRD
E.coli LPAAT    251 CVSTIS----  NKINLNRIHN GLVIVEMLPP  IDVSQGKDQ   VRELAAHCR-
H.influenzae    251 VCSSTH----  NKINLNRWDN GKVICEIMDP  DDVSGYTKDN  VRDLAAYCHF
S.typhimuriu    251 CVSNIS----  NKVNLNRINN GLVIVEMLPP  VDVSEYGKDQ  VRELAAHCRF
L.douglassi     251 ILTGTHLAWF  TRKGIFRVRP VPITVKYLPP  INTDDWTVDK  IDDYVKMIHD
C. nucifera     251 VLTGTHLAW-  -RKNSLRVRP APITVKYFSP IKTDDWEEK   INHYVEMIHF
```

Figure 5 (continued)

|  |  | 310 | 320 | 330 | 340 | 350 |
|---|---|---|---|---|---|---|
| Human LPAAT-β | 301 | AMRTIFIHIS | KTPQENGATA | GSGVQPAQ* | | |
| Human LPAAT-α | 301 | SMLTVFREIS | TDGRGGDYL | KKPGGG*— | | |
| Yeast LPAAT | 301 | QMVDILKEIG | YSPAINDTTL | PPQAIEYAAL | QHDKKVNKKI | KNEPVPSVSI |
| E.coli LPAAT | 301 | -SIMEQKIAE | LDKEVA--ER | EAAGKV*— | | |
| H.influenzae | 301 | TDLMEKRIAE | LDEEIA---- | ---KGN*— | | |
| S.typhimuriu | 301 | TALMEQKIAE | LDKEVA--ER | EATGKV*— | | |
| L.douglassi | 301 | IYVRNLPASQ | KPLGS--TNR | --S-K*— | | |
| C. nucifera | 301 | TALYVDHLPE | SQKPLVSKGR | DASGRSNS*- | | |

|  |  | 360 | 370 | 380 | 390 |
|---|---|---|---|---|---|
| Human LPAAT-β | 351 | ---------- | ---------- | ---------- | ...... |
| Human LPAAT-α | 351 | ---------- | ---------- | ---------- | ...... |
| Yeast LPAAT | 351 | SNDVNIHNEG | SSVKKMH*... | | |
| E.coli LPAAT | 351 | ---------- | ---------- | ---------- | ...... |
| H.influenzae | 351 | ---------- | ---------- | ---------- | ...... |
| S.typhimuriu | 351 | ---------- | ---------- | ---------- | ...... |
| L.douglassi | 351 | ---------- | ---------- | ---------- | ...... |
| C. nucifera | 351 | ---------- | ---------- | ---------- | ...... |

TLC Analysis of Acyltransferase Acitvity

> # MAMMALIAN LYSOPHOSPHATIDIC ACID ACYLTRANSFERASE

TECHNICAL FIELD OF THE INVENTION

This present invention provides cDNA sequences and polypeptides having the enzyme lysophosphatidic acid acyltransferase (LPAAT) activity. LPAAT is also known as 1-acyl sn-glycerol-3-phosphate acyltransferase. The present invention further provides for isolation and production of polypeptides involved in phosphatidic acid metabolism and signaling in mammalian cells, in particular, the production of purified forms of LPAAT.

BACKGROUND OF THE INVENTION

Originally regarded as intermediates in lipid biosynthesis (Kent, *Anal. Rev. Biochem.* 64:315–343, 1995), phosphatidic acid (PA) and one of its precursors, lysophosphatidic acid (LPA), have also been identified as phospholipid signaling molecules that affect a wide range of biological responses (McPhail et al., *Proc. Natl. Acad. Sci. USA* 92:7931–7935, 1995; Williger et al., *J. Biol. Chem.* 270:29656–29659, 1995; Moolenaar, *Curr. Opin. Cell Biol.* 7:203–210, 1995).

Cellular activation in monocytic and lymphoid cells is associated with rapid upregulation of synthesis of phospholipids (PL) that includes phosphatidic acid (PA), diacylglycerol (DAG) and glycan phosphatidylinositol (PI). Phosphatidic acids (PA) are a molecularly diverse group of phospholipid second messengers coupled to cellular activation and mitogenesis (Singer et al., *Exp. Opin. Invest. Drugs* 3:631–643, 1994). Compounds that would block PA generation and hence diminish the signal involved in cell activation may therefore be of therapeutic interest in the area of inflammation and oncology. Lysofylline (1-(R)-(5-hydroxyhexyl)-3,7-dimethylxanthine) (Singer et al., *Exp. Opin. Invest. Drugs* 3:631–643, 1994; and Rice et al., *Proc. Natl. Acad. Sci. USA* 91:3857–3861, 1994) has been found to be an effective inhibitor of cellular activation by blocking the synthesis of a specific phosphatidic acid (PA) species produced by lysophosphatidic acid acyltransferase (LPAAT) in activated monocytic cells (Rice et al., *Proc. Natl. Acad. Sci. USA* 91:3857–3861, 1994). PA can be generated through hydrolysis of phosphatidylcholine (PC) (Exton, *Biochim. Biophys. Acta* 1212:26–42, 1994) or glycan PI (Eardley et al., *Science* 251:78–81, 1991; Merida et al., *DNA Cell Biol.* 12:473–479, 1993), through phosphorylation of DAG by DAG kinase (Kanoh et al., *Trends Biochem. Sci.* 15:47–50, 1990) or through acylation of LPA at the SN2 position (Bursten et al., *Am. J. Physiol.* 266:C1093–C1104, 1994). Compounds that would block PA generation and hence diminish lipid biosynthesis and the signal involved in cell activation may therefore be of therapeutic interest in the area of inflammation and oncology as well as obesity treatment.

The genes coding for LPAAT have been isolated in bacteria (Coleman, *Mol. Gen. Genet.* 232:295–303, 1992), in yeast (Nagiec et al., *J. Biol. Chem.* 268:22156–22163, 1993) and in plants (Brown et al., *Plant Mol. Biol.* 26:211–223, 1994; and Hanke et al., *Eur J. Biochem.* 232:806–810, 1995) using genetic complementation techniques. The cloning of a mammalian version of LPAAT has not been reported. Homology among the bacterial, yeast and plant LPAAT is only found in a very few block of three or at most four amino acids scattered throughout the sequences (Brown et al., *Plant Mol. Biol.* 26:211–223, 1994). Further, there is a need in the art for recombinant LPAAT from a mammalian source to enable compound screening for LPAAT inhibitors for the development of specific compounds that would inhibit this enzyme.

SUMMARY OF THE INVENTION

The present invention provides a cDNA sequence, polypeptide sequence, and transformed cells for producing isolated recombinant mammalian LPAAT. The present invention provides two novel human polypeptides, and fragments thereof, having LPAAT activity. The polypeptides discovered herein is novel and will be called hLPAAT with the first one discovered designated hLPAATα and the second one discovered called hLPAATβ. LPAAT catalyzes the acylation of lysophosphatidic acid (LPA) to phosphatidic acid (PA) by acylating the sn-2 position of LPA with a fatty acid acyl-chain moiety.

The present invention further provides nucleic acid sequences coding for expression of the novel LPAAT polypeptides and active fragments thereof. The invention further provides purified LPAATs and antisense oligonucleotides for modulation of expression of the genes coding for LPAAT polypeptides. Assays for screening test compounds for their ability to inhibit LPAATs are also provided.

Recombinant LPAAT is useful for screening candidate drug compounds that inhibit LPAAT activity. The present invention provides cDNA sequences encoding a polypeptide having LPAAT activity and comprising the DNA sequence set forth in SEQ ID NO. 1 of SEQ ID NO. 7, shortened fragments thereof, or additional cDNA sequences which due to the degeneracy of the genetic code encode a polypeptide of SEQ ID NO. 2 or SEQ. ID NO. 8 or biologically active fragments thereof or a sequence capable of hybridizing thereto under high stringency conditions. The present invention further provides a polypeptide having LPAAT activity and comprising the amino acid sequence of SEQ ID NO. 2 or SEQ ID NO. 8 or biologically active fragments thereof.

Also provided by the present invention are vectors containing a DNA sequence encoding a mammalian LPAAT enzyme in operative association with an expression control sequence. Host cells, transformed with such vectors for use in producing recombinant LPAAT, are also provided with the present invention. The inventive vectors and transformed cells are employed in a process for producing recombinant mammalian LPAAT. In this process, a cell line transformed with a DNA sequence encoding on expression for a LPAAT enzyme in operative association with an expression control sequence, is cultured. The claimed process may employ a number of known cells as host cells for expression of the LPAAT polypeptide, including, for example, mammalian cells, yeast cells, insect cells and bacterial cells.

Another aspect of this invention provides a method for identifying a pharmaceutically-active compound by determining if a selected compound is capable of inhibiting the activity of LPAAT for acylating LPA to PA. A compound capable of such activity is capable of indirectly inhibiting SAPkinase and being a pharmaceutical compound useful for augmenting trilineage hematopoiesis after cytoreductive therapy and for anti-inflammatory activity in inhibiting the inflammatory cascade following hypoxia and reoxygenation injury (e.g., sepsis, trauma, ARDS, etc.).

The present invention further provides a transformed cell that expresses active mammalian LPAAT and further comprises a means for determining if a drug candidate compound is therapeutically active by inhibiting recombinant LPAAT activity.

BRIEF DESCRIPTION OF THE DRAWINGS

FIG. 1 shows the DNA sequence of the cDNA insert of pZplat.11 encoding hLPAATα.

FIG. 2 shows amino acid sequence alignment of the human LPAATα coding sequence, the yeast LPAAT coding sequence, E. coli LPAAT coding sequence, and the maize LPAAT coding sequence. This comparison shows that human LPAATα has the greatest extended homology with yeast or E. coli LPAAT than with the plant LPAAT.

FIG. 3 shows the DNA sequence of the cDNA insert pSP.LPAT3 encoding hLPAATβ. The nucleotide sequence analysis and restriction mapping of the cDNA clone revealed a 5' untranslated region of 39 base pairs and an open reading frame encoding a 278 amino acid polypeptide that spans positions 40–876. It also shows a 3' untranslated region of 480 base pairs from pSP.LPAT3. The initiation site for translation was localized at nucleotide positions 40–42 and fulfilled the requirement for an adequate initiation site (Kozak, *Critical Rev. Biochem. Mol. Biol.* 27:385–402, 1992).

FIG. 4 shows the sequence of the hLPAATβ 278 amino acid open reading frame. The amino acid sequence was used as the query sequence to search for homologous sequences in protein databases. Search of the database based on Genbank Release 92 from the National Center for Biotechnology Information (NCBI) using the blastp program showed that this protein was most homologous to the yeast, bacterial and plant LPAATs.

FIG. 5 shows amino acid sequences alignment of this putative human LPAATβ coding sequence, human LPAATα coding, the yeast LPAAT coding sequence, the bacterial (*E. coli, H. influenzae,* and *S. typhimurium*) LPAAT coding sequences, and the plant (*L. douglassi* and *C. nucifera*) LPAAT coding sequences, revealing that the human LPAAT coding sequences have a much more extended homology with the yeast or the bacterial LPAAT than with the plant LPAAT.

DETAILED DESCRIPTION OF THE INVENTION

Figure 6:
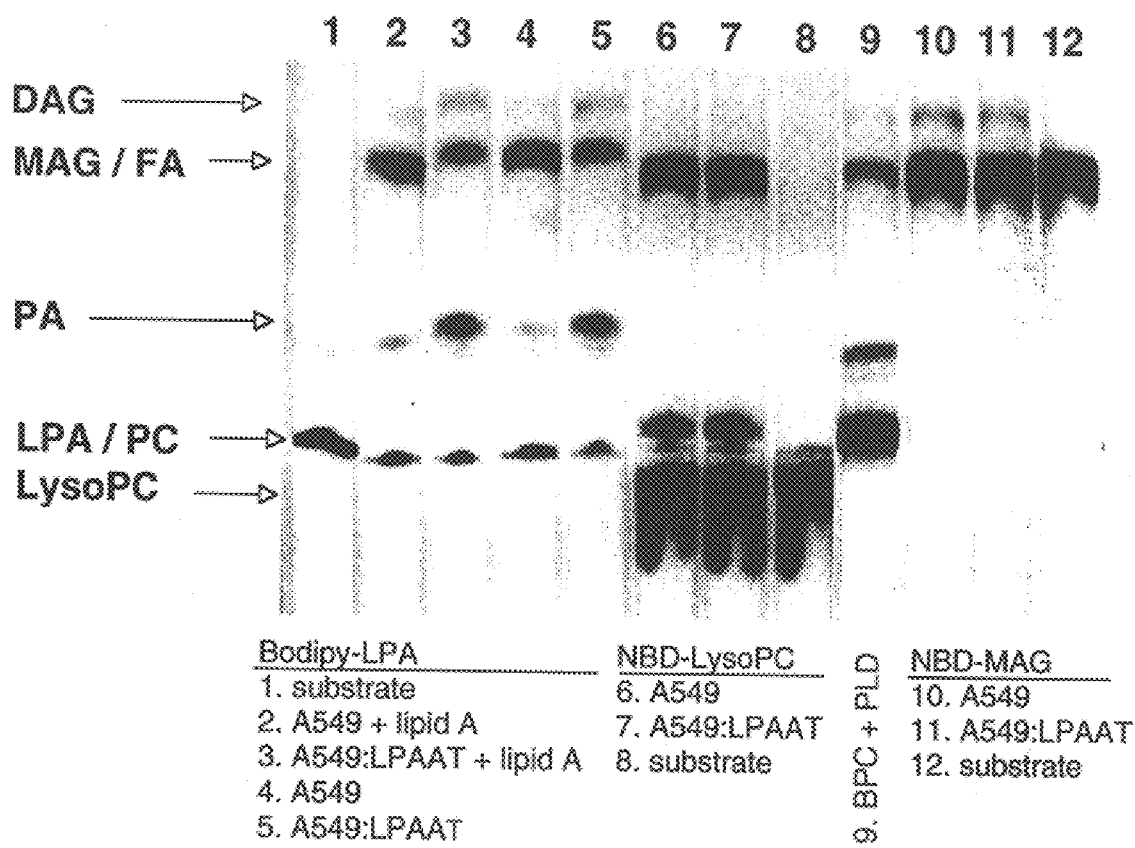
FIG. 6 shows a comparison of LPAAT activity in A549 cells transfected with pCE9.LPAAT1 DNA, or no DNA using a TLC (thin layer chromatography) assay. These data are described in more detail in examples 3 and 4.

The present invention provides novel, isolated, biologically active mammalian LPAAT enzymes. The term "isolated" means any LPAAT polypeptide of the present invention, or any other gene encoding LPAAT polypeptide, which is essentially free of other polypeptides or genes, respectively, or of other contaminants with which the LPAAT polypeptide of gene might normally be found in nature.

The invention includes a functional polypeptide, LPAAT, and functional fragments thereof. As used herein, the term "functional polypeptide" refers to a polypeptide which possesses a biological function or activity which is identified through a biological assay, preferably cell-based, and which results in the formation of PA species from LPA. A "functional polynucleotide" denotes a polynucleotide which encodes a functional polypeptide. Minor modification of the hLPAATα primary amino acid sequence may result in proteins which have substantially equivalent activity as compared to the sequenced hLPAATα polypeptide described herein. Such modifications may be deliberate, as by site-directed mutagenesis, or may be spontaneous. All of the polypeptides produced by these modifications are included herein as long as the acyltransferase activity of LPAAT is present. This can lead to the development of a smaller active molecule which would have broader utility. For example, it is possible to remove amino or carboxy terminal amino acids which may not be required for LPAAT activity.

The hLPAATα and hLPAATβ polypeptide of the present invention also includes conservative variations of the polypeptide sequence. The term "conservative variation" denotes the replacement of an amino acid residue by another, biologically active similar residue. Examples of conservative variations include the substitution of one hydrophobic residue, such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunologically react with the unsubstituted polypeptide.

Polypeptides of the present invention can be synthesized by such commonly used methods as t-BOC or FMOC protection of alpha-amino groups. Both methods involve step-wise syntheses whereby a single amino acid is added at each step starting from the C terminus of the peptide (Coligan et al., *Current Protocols in Immunology,* Wiley Interscience, Unit 9, 1991). In addition, polypeptide of the present invention can also be synthesized by solid phase synthesis methods (e.g., Merrifield, *J. Am. Chem. Soc.* 85:2149, 1962; and Steward and Young, *Solid Phase Peptide Synthesis,* Freeman, San Francisco pp. 27–62, 1969) using copolyol (styrene-divinylbenzene) containing 0.1–1.0 mM amines/g polymer. On completion of chemical synthesis, the ploypeptides can be deprotected and cleaved from the polymer by treatment with liquid HF 10% anisole for about 15–60 min at 0° C. After evaporation of the reagents, the peptides are extracted from the polymer with 1% acetic acid solution, which is then lyophilized to yield crude material. This can normally be purified by such techniques as gel filtration of Sephadex G-15 using 5% acetic acid as a solvent. Lyophilization of appropriate fractions of the column will yield a homogeneous polypeptide or polypeptide derivatives, which are characterized by such standard techniques as amino acid analysis, thin layer chromatography, high performance liquid chromatography, ultraviolet absorption spectroscopsy, molar rotation, solubility and quantitated by solid phase Edman degradation.

The invention also provides polynucleotides which encode the hLPAAT polypeptide of the invention. As used herein, "polynucleotide" refers to a polymer of deoxyribonucleotides or ribonucleotides in the form of a separate fragment or as a component of a larger construct. DNA encoding the polypeptide of the invention can be assembled from cDNA fragments or from oligonucleotides which provide a synthetic gene which is capable of being expressed in a recombinant transcriptional unit. Polynucleotide sequences of the invention include DNA, RNA and cDNA sequences. Preferably, the nucleotide sequence encoding hLPAAT is the sequence of SEQ ID NO. 1 for hLPAATα or SEQ ID NO. 7 for LPAATβ. DNA sequences of the present invention can be obtained by several methods. For example, the DNA can be isolated using hybridization procedures which are known in the art. Such hybridization procedures include, for example, hybridization of probes to genomic of cDNA libraries to detect shared nucleotide sequences, antibody screening of expression libraries to detect shared structural features, such as a common antigenic epitope, and synthesis by the polymerase chain reaction (PCR).

Hybridization procedures are useful for screening of recombinant clones by using labeled mixed synthetic oligonucleotides probes, wherein each probe is potentially the complete complement of a specific DNA sequence in a hybridization sample which includes a heterogeneous mixture of denatured double-stranded DNA. For such screening, hybridization is preferably performed on either single-stranded DNA or denatured double-stranded DNA. Hybridization is particularly useful for detection of cDNA clones derived from sources where an extremely low amount of mRNA sequences relating to the polypeptide of interest are present. Using stringent hybridization conditions directed to avoid non-specific binding, it is possible to allow an autoradiographic visualization of a specific cDNA clone by the hybridization of the target DNA to that single probe in the mixture, which is its complement (Wallace et al. *Nucl. Acid Res.* 9:879, 1981). The development of specific DNA sequences encoding hLPAAT can also be obtained by isolation of double-stranded DNA sequences from the genomic DNA, chemical manufacture of a DNA sequence to provide the necessary codons for the polypeptide of interest, and in vitro synthesis of a double-stranded DNA sequence by reverse transcription of mRNA isolated for a eukaryotic donor cell. In the latter case, a double-stranded DNA complement of MRNA is eventually formed which is generally referred to as cDNA. Of these three methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently a method that is preferred when the entire sequence of amino acids residues of the desired polypeptide product is known. When the entire sequence of amino acid residues of the desired polypeptide is not known, direct synthesis of DNA sequences is not possible and it is desirable to synthesize cDNA sequences. cDNA sequence isolation can be done, for example, by formation of plasmid- or phage-carrying cDNA libraries which are derived from reverse transcription of MRNA. mRNA is abundant in donor cells that have high levels of genetic expression. In the event of lower levels of expression, PCR techniques are preferred. When a significant portion of the amino acid sequence is known, production of labeled single or double stranded DNA or RNA probe sequences duplicating a sequence putatively present in the target cDNA may be employed in DNA/DNA hybridization procedures, carried out on cloned copies of the cDNA (denatured into a single-stranded form) (Jay et al., *Nucl. Acid Res.* 11:2325, 1983).

A cDNA expression library, such as lambda gt11, can be screened indirectly for hLPAATα or hLPAATβ polypeptide having at least one epitope, using antibodies specific for hLPAATα or hLPAATβ. Such antibodies can be either polyclonally or monoclonally derived and used to detect expression product indicative of the presence of hLPAATα or hLPAATβ cDNA.

A polynucleotide sequence can be deduced from the genetic code, however the degeneracy of the code must be taken into account. Polynucleotides of this invention include sequences which are degenerate as a result of the genetic code. The polynucleotides of this invention also include sequences that are degenerate as a result of the genetic code. There are 20 natural amino acids, most of which are specified by more that one codon (a three base sequence). Therefore, as long as the amino acid sequences of hLPAATα and hLPAATβ results in a functional polypeptide (at least, in the case of the sense polynucleotide strand), all degenerate nucleotide sequences are included in the invention. The polynucleotide sequence for hLPAATα and hLPAATβ also includes sequences complementary to the polynucleotides encoding hLPAATα and hLPAATβ (antisense sequences). Antisense nucleic acids are DNA and RNA molecules that are complementary to at least a portion of a specific mRNA molecule (Weintraub, *Sci. Amer.* 262:40, 1990). The invention embraces all antisense polynucleotides capable of inhibiting the production of hLPAATα and hLPAATβ polypeptide. In the cell, the antisense nucleic acids hybridize to the corresponding mRNA, forming a double-stranded molecule. The antisense nucleic acids interfere with the translation of mRNA since the cell cannot translate mRNA that is double-stranded. Antisense oligomers of about 15 nucleotides are preferred, since they are easily synthesized and are less likely to cause problems than larger molecules when introduced into the target hLPAATα and hLPAATβ-producing cell. The use of antisense methods to inhibit translation of genes is known (e.g., Marcus-Sakura, *Anal. Biochem.* 172:289, 1988).

In addition, ribozyme nucleotide sequences for hLPAATα and hLPAATβ are included in this invention. Ribozymes are RNA molecules possessing an ability to specifically cleave other single-stranded RNA in a manner analogous to DNA restriction endonucleases. Through the modification of nucleotide sequences which encode such RNAs, it is possible to engineer molecules that recognize specific nucleotide sequences in an RNA molecule and cleave it (Cech, *J. Amer. Med. Assn.* 260:3030, 1988). An advantage of this approach is that only mRNAs with particular sequences are inactivated because they are sequence-specific.

There are two basic types of ribozymes, tetrahymena-type (Hasselhoff, *Nature* 334:585, 1988) and "hammerhead-type". Tetrahymena-type ribozymes recognize sequences which are four bases in length, while "hammerhead-type" ribozymes recognize base sequences 11–18 bases in length. The longer the recognition sequence, the greater the likelihood that the sequence will occur exclusively in the target MRNA species. Consequently, hammerhead-type ribozymes are preferable to tetrahymena-type ribozymes for inactivating a specific mRNA species.

Polynucleotide sequences encoding the hLPAATα and hLPAATβ polypeptides of the invention can be expressed in either prokaryotes or eukaryotes. Hosts can include microbial (bacterial), yeast, insect and mammalian organisms. Methods of expressing DNA sequences having eukaryotic or viral sequences in prokaryotes are known in the art. Biologically functional viral and plasmid DNA vectors capable of expression and replication in a host are known in the art. Such vectors are used to incorporate DNA sequences of the invention. DNA sequences encoding the inventive polypeptides can be expressed in vitro by DNA transfer into a suitable host using known methods of transfection.

The hLPAATα and hLPAATβ DNA sequences may be inserted into a recombinant expression vector. The term "recombinant expression vector" refers to a plasmid, virus or other vehicle that has been manipulated by insertion or incorporation of the genetic sequences. Such expression vectors contain a promoter sequence which facilitates efficient transcription of the inserted genetic sequence of the host. The expression vector typically contains an origin of replication, a promoter, as well as specific genes which allow phenotypic selection of the transformed cells. Vectors suitable for use in the present invention include, for example, with bacterial promoter and ribosome binding site expression vector for expression in bacteria (Gold, *Meth. Enzymol.* 185:11, 1990), expression vector with animal promoter and enhancer for expression in mammalian cells (Kaufman, *Meth. Enzymol.* 185:487, 1990) and baculovirus-derived vectors for expression in insect cells (Luckow et al., *J. Virol.* 67:4566, 1993). The DNA segment can be present in the vector operably linked to regulatory elements, for example, a promoter (e.g., T7, metallothionein I, or polyhedren promoters).

The vector may include a phenotypically selectable marker to identify host cells which contain the expression vector. Examples of markers typically used in prokaryotic expression vectors include antibiotic resistance genes for ampicillin (β-lactamases), tetracycline and chloramphenicol (chloramphenicol acetyltransferase). Examples of such markers typically used in mammalian expression vectors include the gene for adenosine deaminase (ADA), aminoglycoside phosphotransferase (neo, G418), dihydrofolate reductase (DHFR), hygromycin-B-phosphotransferase (HPH), thymidine kinase (TK), and xanthine guanine phosphoriboseyltransferase (XGPRT, gpt).

In another preferred embodiment, the expression system used is one driven by the baculovirus polyhedrin promoter. The gene encoding the polypeptide can be manipulated by standard techniques in order to facilitate cloning into the baculovirus vector. See Ausubel et al., supra. A preferred baculovirus vector is the pBlueBac vector (Invitrogen, Sorrento, Calif.). The vector carrying the gene for the polypeptide is transfected into *Spodoptera frugiperda* (Sf9) cells by standard protocols, and the cells are cultured and processed to produce the recombinant polypeptide. See Summers et al., *A Manual for Methods of Baculovirus Vectors and Insect Cell Culture Procedures,* Texas Agricultural Experimental Station.

Once the entire coding sequence of the gene for the polypeptides has been determined, the gene can be inserted into an appropriate expression system. The gene can be expressed in any number of different recombinant DNA expression systems to generate large amounts of polypeptide. Included within the present invention are polypeptides having native glycosylation sequences, and deglycosylated or unglycosylated polypeptides prepared by the methods described below. Examples of expression systems known to the skilled practitioner in the art include bacteria such as *E. coli,* yeast such as *Pichia pastoris,* baculovirus, and mammalian expression systems such as in Cos or CHO cells.

The gene or gene fragment encoding the desired polypeptide can be inserted into an expression vector by standard subcloning techniques. In a preferred embodiment, an *E. coli* expression vector is used which produces the recombinant protein as a fusion protein, allowing rapid affinity purification of the protein. Examples of such fusion protein expression systems are the glutathione S-transferase system (Pharmacia, Piscataway, N.J.), the maltose binding protein system (NEB, Beverley, Mass.), the thiofusion system (Invotrogen, San Diego, Calif.), the FLAG system (IBI, New Haven, Conn.), and the 6xHis system (Qiagen, Chatsworth, Calif.). Some of these systems produce recombinant polypeptides bearing only a small number of additional amino acids, which are unlikely to affect the LPAAT ability of the recombinant polypeptide. For example, both the FLAG system and the 6xHis system add only short sequences, both of which are known to be poorly antigenic and which do not adversely affect folding of the polypeptide to its native conformation. Other fusion systems produce proteins where it is desirable to excise the fusion partner from the desired protein. In a preferred embodiment, the fusion partner is linked to the recombinant polypeptide by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.) or enterokinase (Invotrogen, San Diego, Calif.).

Production of Polypeptides

In a preferred embodiment, recombinant proteins are expressed in *E. coli* and in baculovirus expression systems. The complete gene for the polypeptide can be expressed or, alternatively, fragments of the gene encoding antigenic determinants can be produced. In a first preferred embodiment, the gene sequence encoding the polypeptide is analyzed to detect putative transmembrane sequences. Such sequences are typically very hydrophobic and are readily detected by the use of standard sequence analysis software, such as MacDNASIS (Hitachi, San Bruno, Calif.). The presence of transmembrane sequences is often deleterious when a recombinant protein is synthesized in many expression systems, especially *E. coli,* as it leads to the production of insoluble aggregates which are difficult to renature into the native conformation of the polypeptide. Deletion of transmembrane sequences typically does not significantly alter the conformation of the remaining polypeptide structure. Moreover, transmembrane sequences, being by definition embedded within a membrane, are inaccessible as antigenic determinants to a host immune system. Antibodies to these sequences will not, therefore, provide immunity to the host and, hence, little is lost in terms of immunity by omitting such sequences from the recombinant polypeptides of the invention. Deletion of transmembrane-encoding sequences from the genes used for expression can be achieved by standard techniques. See Ausubel et al., supra, Chapter 8. For example, fortuitously-placed restriction enzyme sites can be used to excise the desired gene fragment, or the PCR can be used to amplify only the desired part of the gene.

Transformation of a host cell with recombinant DNA may be carried out by conventional techniques. When the host is prokaryotic, such as *E. coli,* competent cells which are capable of DNA uptake can be prepared from cells harvested after exponential growth phases and subsequently treated by a $CaCl_2$ method using standard procedures. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures, such as microinjection, electroporation, insertion of a plasmid encased in a liposome, or virus vectors may be used. Eukaryotic cells can also be cotransformed with DNA sequences encoding the hLPAATα and hLPAATβ polypeptides of the invention, and a second foreign DNA molecule encoding a selectable phenotype, such as the herpes simplex thymidine kinase gene. Another method uses a eukaryotic viral vector, such as simian virus 40 (SV40) or bovine papilloma virus to transiently infect or transform eukaryotic cells and express the hLPAATα and hLPAATβ polypeptides.

Expression vectors that are suitable for production of LPAAT polypeptides typically contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; and (3) DNA elements that control the processing of transcripts, such as a transcription termination/polyadenylation sequence. LPAAT polypeptides of the present invention preferably is expressed in eukaryotic cells, such as mammalian, insect and yeast cells. Mammalian cells are especially preferred eukaryotic hosts because mammalian cells provide suitable post-translational modifications such as glycosylation. Examples of mammalian host cells include Chinese hamster ovary cells (CHO-K1; ATCC CCL61), rat pituitary cells (GH$_1$; ATCC CCL82), HeLa S3 cells (ATCC CCL2.2), rat hepatoma cells (H-4-II-E; ATCC CRL1548) SV40-transformed monkey kidney cells (COS-1; ATCC CRL 1650) and murine embryonic cells (NIH-3T3; ATCC CRL 1658). For a mammalian host, the transcriptional and translational regulatory signals may be derived from viral sources, such as adenovirus, bovine papilloma virus, simian virus, or the like, in which the regulatory signals are associated with a particular gene which has a high level of expression. Suitable transcriptional and translational regulatory sequences also can be obtained from mammalian genes, such as actin, collagen, myosin, and metallothionein genes.

Transcriptional regulatory sequences include a promoter region sufficient to direct the initiation of RNA synthesis. Suitable eukaryotic promoters include the promoter of the mouse metallothionein I gene (Hamer et al, *J. Molec. Appl. Genet.* 1:273,1982); the TK promoter of Herpes virus (McKnight, *Cell* 31: 355, 1982); the SV40 early promoter (Benoist et al., *Nature* 290:304, 1981); the Rous sarcoma virus promoter (Gorman et al., *Proc. Nat'l. Acad. Sci.* USA 79:6777, 1982); and the cytomegalovirus promoter (Foecking et al., *Gene* 45:101, 1980). Alternatively, a prokaryotic promoter, such as the bacteriophage T3 RNA polymerase promoter, can be used to control fusion gene expression if the prokaryotic promoter is regulated by a eukaryotic promoter (Zhou et al., *Mol. Cell. Biol.* 10:4529, 1990; Kaufman et al., *Nucl. Acids Res.* 19:4485, 1991).

An expression vector can be introduced into host cells using a variety of techniques including calcium phosphate transfection, liposome-mediated transfection, electroporation, and the like. Preferably, transfected cells are selected and propagated wherein the expression vector is stably integrated in the host cell genome to produce stable transformants. Techniques for introducing vectors into eukaryotic cells and techniques for selecting stable transformants using a dominant selectable marker are described, for example, by Ausubel and by Murray (ed.), *Gene Transfer and Expression Protocols* (Humana Press 1991). Examples of mammalian host cells include COS, BHK, 293 and CHO cells.

Purification of Recombinant Polypeptides

The polypeptide expressed in any of a number of different recombinant DNA expression systems can be obtained in large amounts and tested for biological activity. The recombinant bacterial cells, for example *E. coli,* are grown in any of a number of suitable media, for example LB, and the expression of the recombinant polypeptide induced by adding IPTG to the media or switching incubation to a higher temperature. After culturing the bacteria for a further period of between 2 and 24 hours, the cells are collected by centrifugation and washed to remove residual media. The bacterial cells are then lysed, for example, by disruption in a cell homogenizer and centrifuged to separate the dense inclusion bodies and cell membranes from the soluble cell components. This centrifugation can be performed under conditions whereby the dense inclusion bodies are selectively enriched by incorporation of sugars such as sucrose into the buffer and centrifugation at a selective speed. If the recombinant polypeptide is expressed in the inclusion, these can be washed in any of several solutions to remove some of the contaminating host proteins, then solubilized in solutions containing high concentrations of urea (e.g., 8M) or chaotropic agents such as guanidine hydrochloride in the presence of reducing agents such as β-mercaptoethanol or DTT (dithiothreitol). At this stage it may be advantageous to incubate the polypeptide for several hours under conditions suitable for the polypeptide to undergo a refolding process into a conformation which more closely resembles that of the native polypeptide. Such conditions generally include low polypeptide (concentrations less than 500 mg/ml), low levels of reducing agent, concentrations of urea less than 2M and often the presence of reagents such as a mixture of reduced and oxidized glutathione which facilitate the interchange of disulphide bonds within the protein molecule. The refolding process can be monitored, for example, by SDS-PAGE or with antibodies which are specific for the native molecule. Following refolding, the polypeptide can then be purified further and separated from the refolding mixture by chromatography on any of several supports including ion exchange resins, gel permeation resins or on a variety of affinity columns.

Isolation and purification of host cell expressed polypeptide, or fragments thereof may be carried out by conventional means including, but not limited to, preparative chromatography and immunological separations involving monoclonal or polyclonal antibodies.

These polypeptides may be produced in a variety of ways, including via recombinant DNA techniques, to enable large scale production of pure, active hLPAATα and hLPAATβ useful for screening compounds for trilineage hematopoietic and anti-inflammatory therapeutic applications, and developing antibodies for therapeutic, diagnostic and research use.

The hLPAATα and hLPAATβ polypeptides of the present invention are useful in a screening methodology for identifying compounds or compositions which affect cellular signaling of an inflammatory response. This method comprises incubating the hLPAATα and hLPAATβ polypeptides or a cell transfected with cDNA encoding hLPAATα and hLPAATβ under conditions sufficient to allow the components to interact, and then measuring the effect of the compound or composition on hLPAATα and hLPAATβ activity. The observed effect on hLPAATα and hLPAATβ may be either inhibitory or stimulatory.

hLPAATα

Search of the Genbank database of expressed sequence tag (dbest) using either the yeast or plant LPAAT protein sequences as probe came up with several short stretches of cDNA sequences with homology to the yeast or plant LPAAT protein sequence. These cDNA sequences of interest were derived from single-run partial sequencing of random human cDNA clones projects carried out by either the WashU-Merck EST or the Genexpress-Genethon program. An example of the amino acids sequence homology between the yeast LPAAT and a human cDNA clone (dbest#102250) is shown below by comparing SEQ ID NO. 3 (top amino acid sequence) with SEQ ID NO 4 (bottom amino acid sequence):

```
PFKKGAFHLAQQGKIPIVPVVVSNTSTLVSPKYGVFNRGCMIVRILKPISTE

*   ******  *  ****  *  *       *   *   *    **  *  *  **

PSNCGAFHLAVQAQVPIVPIVMSSYQDFYCKKERRFTSGQCQVRVLPPVPTE
```

The top line refers to the yeast LPAAT sequence from amino acids 169 to 220 and the bottom line refers to the homologous region from the dbest clone#102250. Identical amino acids between these two sequences are shown in block letters with asterisks in between.

Accordingly, a synthetic oligonucleotide (o.BLPAT.2R), 5'-TGCAAGATGGAAGGCGCC-3' (SEQ ID NO. 5), was made based on the complement sequence of the conserved amino acids region, GAFHLA (SEQ ID NO. 6), of clone#102250. o.BPLAT.2R was radiolabeled at its 5'-end using $\gamma$-$^{32}$P-ATP and T4 polynucleotide kinase as a probe in screening a λzap human brain cDNA library (Stratagene).

Screening of the cDNA library was accomplished by filter hybridization using standard methods (*Current Protocols in Molecular Biology*, John Wiley & Sons, Inc., 1995). Duplicate filters containing DNA derived from X phage plagues were prehybridized at 60° C. for 2 hr in 6× SSC (1× SSC is 0.15M NaCl, 0.015M sodium citrate, pH 7.0), 5× Denhardt's solution (1× Denhardt's solution is 0.02% Ficoll, 0.02% bovine serum albumin, and 0.02% polyvinyl-pyrrolidone), 0.1 % sodium dodecyl sulfate (SDS), 50 mg/ml sonicated and denatured salmon sperm DNA. Hybridization was carried out in the same buffer as used for prehybridzation. After hybridization, the filters were washed in 6× SSC at 42° C., and autoradiographed.

Of the approximately 1×10$^6$ clones from the human brain cDNA library that were screened, twelve clones were identified that hybridized with the probe in duplicate filters. Eleven out twelve clones were enriched and recovered after a secondary screen. Ten enriched phage samples were then converted to plasmid transformed cells by co-infecting *E. coli* XL1-Blue with the helper phage R408 using Stratagene's recommended procedure. Colony filter hybridization was performed and identified those colonies that "lit up" with the probe. Seven out of the ten pools of colonies contained positive clones. Two out of these seven clones, pZlpat.10 and pZlpat.11, contained inserts >2 kb. Restriction mapping using a combination of Sst I, Pst I and BamHI digests showed these two clones contained many common fragments with respect to each other.

Nucleotide sequencing of the cDNA inserts in pZlpat.10 and pZlpat.11 was performed. FIG. 1 shows the DNA sequence of the cDNA insert of pZplat.11. The nucleotide sequence analysis and restriction mapping of the cDNA clone revealed a 5'-untranslated region of >300 bp, an open reading frame capable of encoding a 283 amino acid polypeptide, and a 3'-untranslated region of >800 bp. The initiation site for translation was localized at nucleotide positions 319–321 and fulfilled the requirement for an adequate initiation site according to Kozak (Kozak, *Critical Rev. Biochem. Mol. Biol.* 27:385–402, 1992). There was another upstream ATG at positions 131–133 with an in-phase stop codon at positions 176–178. Except with a shorter 5'-untranslated region, the cDNA insert of pZplat. 10 has the same DNA sequence as that of pZplat.11.

The sequence of the 283 amino acid open reading frame in pZplat.11 was used as the query sequence to search for homologous sequences in protein databases. Search of the database based on Genbank Release 90 from the National Center for Biotechnology Information (NCBI) using the blastp program showed that the protein encoded by pZplat.11 was most homologous to the yeast and bacterial LPAATs. FIG. 2 shows amino acid sequences alignment of the putative human LPAATα coding sequence, the yeast LPAAT coding sequence, the *E. coli* LPAAT coding sequence, and the maize LPAAT coding sequence, revealing that human LPAATα has a much more extended homology with the yeast or the *E. coli* LPAAT than with the plant LPAAT.

hLPAATβ

Search of the Genbank database (Boguski, et al., *Science* 265:1993–1994, 1994) of expressed sequence tag (dbEST) using either the yeast or plant LPAAT protein sequences as probe came up with several short stretches of cDNA sequences with homology to the yeast or plant LPAAT protein sequence. These cDNA sequences of interest were derived from single-run partial sequencing of random human cDNA clones projects carried out mainly by I.M.A.G.E. Consortium [LLNL] cDNA clones program. An example of the amino acids sequence homology between the yeast LPAAT and a human cDNA clone (dbEST#363498) is shown below:

```
        180       190       200       210       220       230
        QQGKIPIVPVVVSNTSTLVSPKYGVFNRGCMIVRILKPISTENLTKDKIGEFAEKVRDQM
         ....::::::  :.  :...  ...:    :...:  ..:...:...:..:::  ....  ..
        VRENVPIVPVVYSSFSSFYNTKKKFFTSGTVTVQVLEAIPTSGLTAADVPALRGTPATGP
         70        80        90        100       110       120
```

The top line refers to the yeast LPAAT sequence from amino acids 171 to 230 (SEQ ID NO. 9) and the bottom line refers to the homologous region from the dbest clone#363498 using the +1 reading frame (SEQ ID NO. 10). Identical and conserved amino acids between these two sequences are shown with double dots and single dot, respectively, in between. In order to find out if such cDNA clones with limited homology to yeast LPAAT sequence indeed encode human LPAATβ sequence, it was necessary to isolate the full-length cDNA clone, insert it into an expression vector, and to test if cells transformed or transfected with the cDNA expression vector produced more LPAAT activity.

Accordingly, two synthetic oligonucleotides, 5'-CCTCAAAGTG TGGATCTATC-3' (o.LPAT3.F) (SEQ ID NO. 11) and 5'-GGAAGAGTAC ACCACGGGGA C-3' (o.LPAT3.R), (SEQ ID NO. 12) were ordered (Life Technologies, Gaithersburg, Md.) based on, respectively, the coding and the complement sequence of clone#363498. o.LPAT3.R was used in combination with a forward vector primer (o.sport.1), 5'- GACTCTAGCC TAGGCTTTTG C-3' (SEQ ID NO. 13) for amplification of the 5'-region, while o.LPAT3.F was used in combination with a reverse vector primer (o.sport.1R), 5'-CTAGCTTATA ATACGACTCA C-3' (SEQ ID NO. 14), for amplification of the 3'-region of potential LPAATβ sequences from a pCMV.SPORT human leukocyte cDNA library (Life Technologies, Gaithersburg, Md.). A 700 bp PCR fragment derived from o.sport.1 and o.LPAT3.R amplification was cut with EcoR I before inserting in between the Sma I and EcoR I of pBluescript(II)SK(−) (Stratagene, LaJolla, Calif.) to generate pLPAT3.5'. A 900 bp PCR fragment derived from o.sport. 1R and o.LPAT3.F amplification was cut with Xba I before inserting in between the Sma I and Xba I of pBluescript(II)SK(−) (Stratagene, LaJolla, Calif.) to generate pLPAT3.3'. Nucleotide sequencing analysis of the cDNA inserts from these two plasmids showed they contained overlapping sequences with each other, sequences that matched with the dbEST#363498 as well as extensive homology with the yeast LPAAT amino acids sequence (Nagiec et al., *J. Biol. Chem.* 268:22156–22163, 1993). To assemble the two halves of the cDNA into a full-length clone, the 560 bp Nco I—Nar I fragment from pLPAT3.5' and the 780 bp Nar I—Xba I fragment from pLPAT3.3' were inserted into the Nco I/Xba I vector prepared from pSP-luc+ (Promega, Madison, Wis.) via a three-part ligation to generate pSP.LPAT3.

FIG. 3 shows the DNA sequence ID of the cDNA insert of pSP.LPAT3. The nucleotide sequence analysis and restriction mapping of the cDNA clone revealed a 5'-untranslated region of 39 bp, an open reading frame capable of encoding a 278 amino acids polypeptide that spans nucleotide positions 40 to 876 and a 3'-untranslated region of 480 bp (FIG. 3). The initiation site for translation was localized at nucleotide positions 40–42 and fulfilled the requirement for an adequate initiation site according to Kozak (Kozak, *Critical Rev. Biochem. Mol. Biol.* 27:385–402, 1992).

The sequence of the 278 amino acid open reading frame (FIG. 4) was used as the query sequence to search for homologous sequences in protein databases. Search of the database based on Genbank Release 92 from the National Center for Biotechnology Information (NCBI) using the blastp program showed that this protein was most homologous to the yeast, bacterial and plant LPAATs. FIG. 5 shows amino acid sequences alignment of this putative human LPAATβ coding sequence, human LPAATα coding, the yeast LPAAT coding sequence, the bacterial (*E. coli, H. influenzae,* and *S. typhimurium*) LPAAT coding sequences, and the plant (*L. douglassi* and *C. nucifera*) LPAAT coding sequences, revealing that the human LPAAT coding sequences have a much more extended homology with the yeast or the bacterial LPAAT than with the plant LPAAT.
Characterization of the Invention Accordingly, human LPAATα is characterized by the 283 amino acids of SEQ ID NO. 2. The present invention further includes allelic variations (naturally-occurring base changes in the species population which may or may not result in an amino acid change) of the DNA sequences herein encoding active LPAAT polypeptides and active fragments thereof. The inventive DNA sequences further comprise those sequences which hybridize under high stringency conditions (see, for example, Maniatis et al, *Molecular Coining (A Laboratory Manual)*, Cold Spring Harbor Laboratory, pages 387–389, 1982) to the coding region (e.g., nucleotide #319 to nucleotide #1167). One such high stringency hybridization condition is, for example, 4× SSC at 65° C., followed by washing in 0.1× SSC at 65° C. for thirty minutes. Alternatively, another high stringency hybridization condition is in 50% formamide, 4× SSC at 42° C. The present invention further includes DNA sequences which code for LPAAT polypeptides having LPAAT activity but differ in codon sequence due to degeneracy of the genetic code. Variations in the DNA sequences which are caused by point mutations or by induced modifications of the sequence of SEQ ID NO. 1, which enhance the activity of the encoded polypeptide or production of the encoded LPAAT polypeptide are also encompassed by the present invention.
Definitions In the description that follows, a number of terms are utilized extensively. Definitions are provided to facilitate understanding of the invention.

The term "isolated" applied throughout the specification to polypeptides refers to that level of purity in which the polypeptide is sufficiently free of other materials endogenous to the host from which the polypeptide is isolated such that any remaining materials do not materially affect the biological properties of the polypeptide.

The term "derived" as used throughout the specification in relation to the polypeptides of the present invention, encompasses polypeptides obtained by isolation and purification from host cells, as well as polypeptides obtained by manipulation and expression of nucleotide sequences prepared from host cells. It also encompasses nucleotide sequences including genomic DNA, MRNA, cDNA synthesized from mRNA, and synthetic oligonucleotides having sequences corresponding to the inventive nucleotide sequences. It further encompasses synthetic polypeptide antigens prepared on the basis of the known amino acid sequences of the proteins of the present invention.

The term "expression product" as used throughout the specification refers to materials produced by recombinant DNA techniques.
Peptide sequencing of polypeptides Purified polypeptides prepared by the methods described above can be sequenced using methods well known in the art, for example using a gas phase peptide sequencer (Applied Biosystems, Foster City, Calif.). Because the proteins of the present invention may be glycosylated, it is preferred that the carbohydrate groups are removed from the proteins prior to sequencing. This can be achieved by using glycosidase enzymes. Preferably, glycosidase F (Boehringer-Mannheim, Indianapolis, Ind.) is used. To determine as much of the polypeptide sequence as possible, it is preferred that the polypeptides of the present invention be cleaved into smaller fragments more suitable for gas-phase sequence analysis. This can be achieved by treatment of the polypeptides with selective peptidases, and in a particularly preferred embodiment, with endoproteinase lys-C (Boehringer). The fragments so produced can be separated by reversed-phase HPLC chromatography.

Substitutional variants typically contain the exchange of one amino acid for another at one or more sites within the protein, and are designed to modulate one or more properties of the polypeptides such as stability against proteolytic cleavage. Substitutions preferably are conservative, that is, one amino acid is replaced with one of similar shape and charge. Conservative substitutions are well known in the art and include, for example, the changes of: alanine to serine; arginine to lysine; asparigine to glutamine or histidine; aspartate to glutamate; cysteine to serine; glutamine to asparigine; glutamate to aspartate; glycine to proline; histidine to asparigine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Insertional variants contain fusion proteins such as those used to allow rapid purification of the polypeptide and also can include hybrid polypeptides containing sequences from other proteins and polypeptides which are homologues of the inventive polypeptide. For example, an insertional variant could include portions of the amino acid sequence of the polypeptide from one species, together with portions of the homologous polypeptide from another species. Other insertional variants can include those in which additional amino acids are introduced within the coding sequence of the polypeptides. These typically are smaller insertions than the fusion proteins described above and are introduced, for example, to disrupt a protease cleavage site.

Antibodies to human LPAAT protein can be obtained using the product of an LPAAT expression vector or synthetic peptides derived from the LPAAT coding sequence coupled to a carrier (Pasnett et al., *J. Biol. Chem.* 263:1728, 1988) as an antigen. The preparation of polyclonal antibodies is well-known to those of skill in the art. See, for example, Green et al., "Production of Polyclonal Antisera," in *Immunochemical Protocols* (Manson, ed.), pages 1–5 (Humana Press 1992). Alternatively, an LPAAT antibody of the present invention may be derived from a rodent monoclonal antibody (MAb). Rodent monoclonal antibodies to specific antigens may be obtained by methods known to those skilled in the art. See, for example, Kohler and Milstein, *Nature* 256:495, 1975, and Coligan et al. (eds.), *Current Protocols in Immunology*, 1:2.5.1–2.6.7 (John Wiley & Sons 1991). Briefly, monoclonal antibodies can be obtained by injecting mice with a composition comprising an antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1–2.7.12 and pages 2.9.1–2.9.3. Also, see Baines et al., "Purification of Immunoglobulin G (IgG)," in *Methods in Molecular Biology*, 10:79–104 Humana Press, Inc. 1992. An LPAAT antibody of the present invention may also be derived from a subhuman primate antibody. General techniques for raising therapeutically useful antibodies in baboons may be found, for example, in Goldenberg et al., international patent publication No. WO 91/11465 (1991), and in Losman et al., *Int. J. Cancer* 46:310, 1990.

Alternatively, a therapeutically useful LPAAT antibody may be derived from a "humanized" monoclonal antibody. Humanized monoclonal antibodies are produced by transferring mouse complementary determining regions from heavy and light variable chains of the mouse inununoglobulin into a human variable domain, and then, substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by the publication of Orlandi et al., *Proc. Nat'l. Acad. Sci. USA* 86:3833, 1989. Techniques for producing humanized MAbs are described, for example, by Jones et al., *Nature* 321:522, 1986, Riechmann et al., *Nature* 332:323, 1988, Verhoeyen et al., *Science* 239:1534, 1988, Carter et al., *Proc. Nat'l Acad. Sci. USA* 89:4285, 1992, Sandhu, *Crit. Rev. Biotech.* 12: 437, 1992, and Singer et al., *J. Immun.* 150:2844, 1993, each of which is hereby incorporated by reference.

As an alternative, an LPAAT antibody of the present invention may be derived from human antibody fragments isolated from a combinatorial immunoglobulin library. See, for example, Barbas et al., METHODS: *A Companion to Methods in Enzymology* 2:119 1991, and Winter et al., *Ann. Rev. Immunol.* 12:433, 1994, which are incorporated by reference. Cloning and expression vectors that are useful for producing a human immunoglobulin phage library can be obtained, for example, from STRATAGENE Cloning Systems (La Jolla, Calif.). In addition, an LPAAT antibody of the present invention may be derived from a human monoclonal antibody. Such antibodies are obtained from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13, 1994; Lonberg et al., *Nature* 368:856, 1994, and Taylor et al., *Int. Immun.* 6:579, 1994.

EXAMPLE 1

This example illustrates an experiment to determine if the human LPAATα clone encodes a protein with LPAAT activity, an *E. coli* vector expressing the human LPAATα as a fusion protein with β-galactosidase was transformed into a LPAAT minus strain of *E. coli* to see if it would complement the defect in *E. coli*. Specifically, the 840 bp Bgl II-Nco I fragment, which spans the coding region of human LPAATα from amino acid 68 to beyond the stop codon, derived from pZplat.11 was inserted into a Bgl II/Nco I digested cloning vector pLitmus28 (Evans et al., *BioTechniques* 19:130–135, 1995) to generate the plasmid p28BgN. This plasmid is expected to express the human LPAATα as a fusion protein containing the first 16 amino acids of β-galactosidase and the last 216 residues of the human LPAATα coding sequence using the lac promoter in pLitmus28. This plasmid was transformed into the *E. coli* strain JC201 (obtained from Dr. Jack Coleman, Louisiana State University). JC201 (Coleman, *Mol. Gen. Genet.* 232:295–303, 1992; Nagiec et al., *J. Biol. Chem.* 268:22156–22163, 1993; and Brown et al., *Plant Mol. Biol.* 26:211–223, 1994) is deficient in LPAAT activity due to mutation in the plsC locus. This mutation leads to a temperature-sensitive phenotype that causes JC201 to grow slowly at 37° C., almost not at all at 42° C., and not at all at 44° C. JC201 transformed with p28BgN was able to grow normally at 44° C. when compared to the wild type strain JC200 (plsC⁺), while JC201 transformed with pLitmus28 vector was not able to support growth at 44° C. These data suggest that the putative human LPAATα cDNA isolated here does possess LPAAT activity, as the last 216 amino acids of this cDNA is sufficient to complement the defective LPAAT gene (plsC) in JC201.

EXAMPLE 2

To see if the putative human LPAATβ clone encodes a protein with LPAAT activity, an *E. coli* vector expressing this human LPAATβ as a direct product was transformed into a LPAAT minus strain of E. coli to see if it would complement the defect in E. coli. Specifically, the 1350 bp Nco I—Xba I fragment from pSP.LPAT3, which spans the entire coding region from amino acid 1 to beyond the stop codon, was inserted into a Nco I/Xba I digested cloning vector pKK388-1 (Clontech, Palo Alto, Calif.) to generate the plasmid pTrc.LPAT3. This plasmid was transformed into the E. coli strain JC201 (obtained from Dr. Jack Coleman, Louisiana State University). JC201 (Coleman, *Mol. Gen. Genet.* 232:295–303, 1992) is deficient in LPAAT activity due to mutation in the plsC locus. This mutation leads to a temperature-sensitive phenotype that causes JC201 to grow slowly at 37° C., almost not at all at 42° C., and not at all at 44° C. JC201 transformed with pTrc.LPAT3 was able to grow normally at 44° C. when compared to the wild type strain JC200 (plsC+), while JC201 transformed with pKK388-1 vector was not able to support growth at 44° C. These data suggest that the putative human LPAATβ cDNA isolated here does possess LPAAT activity, as the putative protein product of this cDNA is able to complement the defective LPAAT gene (plsC) in JC201.

EXAMPLE 3

This example illustrates a group of experiments to see if overexpression of this human LPAATα would have any effect on mammalian cells. The entire cDNA insert (~2,300 bp) from pZplat.11 was cleaved with Asp718 I and Xho I for insertion into the mammalian expression vector pCE9 to generate pCE9.LPAAT1. pCE9 was derived from pCE2 with two modifications. The 550 bp BstY I fragment within the elongation factor-1a (EF-1a) intron of pCE2 was deleted. The multiple cloning region of pCE2 between the Asp718 I and BamH I site was replaced with the multiple cloning region spanning the Asp718 I and Bgl II sites from pLitmus28. The plasmid pCE2 was derived from pREP7b (Leung, et al., *Proc. Natl. Acad. Sci. USA*, 92: 4813–4817, 1995) with the RSV promoter region replaced by the CMV enhancer and the elongation factor-1a (EF-1a) promoter and intron. The CMV enhancer came from a 380 bp Xba I-Sph I fragment produced by PCR from pCEP4 (Invitrogen, San Diego, Calif.) using the primers 5'-GGCTCTAGAT ATTAATAGTA ATCAATTAC-3' and 5'-CCTCACGCAT GCACCATGGT AATAGC-3'. The EF-1a promoter and intron (Uetsuki, et al., *J. Biol. Chem.*, 264: 5791–5798, 1989) came from a 1200 bp Sph I-Asp718 I fragment produced by PCR from human genomic DNA using the primers 5'-GGTGCATGCG TGAGGCTCCG GTGC-3' and 5'-GTAGTTTTCA CGGTACCTGA AATGGAAG-3'. These 2 fragments were ligated into a Xba I/Asp718 I digested vector derived from pREP7b to generate pCE2.

pCE9.LPAAT1 DNA was transfected into several mammalian cell lines, including A549 cells, ECV304 cells (American Type Culture Collection, Rockville, Md.), two human cell line that would produce IL-6 and TNF upon stimulation with IL-1b and murine TNF and 293-EBNA cells (Invitrogen, San Diego, Calif.). pCE9.LPAAT1 was digested with BspH I before electroporating into these cell lines with a Cell-Porator™ (Life Technologies, Gaithersburg, Md.) using conditions described previously (Cachianes, et al., *Biotechniques* 15:255–259, 1993). After adherence of the transfected cells 24 hours later, the cells were grown in the presence of 200 μg/ml Hygromycin B (Hyg) (Calbiochem, La Jolla, Calif.) to select for cells that had incorporated both plasmids. Hyg-resistant clones that expressed LPAAT mRNA at a level more than 20 fold higher relative to untranfected cells based on Northern Blot analysis (Kroczek, et al., *Anal. Biochem.* 184: 90–95, 1990) were selected for further study.

FIG. 6 compares the LPAAT activity in A549 cells and in A549 cells transfected with pCE9.LPAAT 1 DNA using aTLC assay. This screening assay for LPAAT activity in cell extracts was based on a fluorecent assay using fluorecent lipid substrates (Ella, et al., *Anal. Biochem.* 218: 136–142, 1994). Instead of using the PC-substrate, BPC (Molecular Probes, Eugene, Oreg.), a synthetic PC that contains an ether linkage at the SN1 position with a fluorescent Bodipy moiety incorporated into the end of the alkyl-chain at the SN1 position, BPC was converted to Bodipy-PA using cabbage phospholipase D (Sigma, St. Louis, Mo.). Bodipy-PA was then converted to Bodipy-LPA using snake venom phospholipase A2. The Bodipy-LPA obtained was purified by preparative TLC for use in the LPAAT assay. The assay was carried out in total cell extracts resuspended in lysis buffer (Ella, et al., *Anal. Biochem.* 218: 136–142, 1994) supplemented with 0.5 mM ATP, 0.3 mM MgCl$_2$, 100 μM oleoyl-CoA and 10 μM Bodipy LPA. The samples were incubated for 30 min before loading onto TLC plates.

Lane 1 refers to Bodipy LPA incubated with buffer only without any cell extract added. Lane 9 refers to BPC treated with cabbage phospholipase D for genereateing a Bodipy-PA marker. Lanes 2 and 4 refer to to Bodipy LPA incubated with control A549 cell extracts with or without lipid A, respectively. Lanes 3 and 5 refer to Bodipy LPA incubated with A549 cell extracts transfected with pCE9.LPAAT1 DNA with or without lipid A, respectively. FIG. 3 shows A549 cells transfected with the LPAAT cDNA (lanes 3 and 5) contain much more LPAAT activity than those of control cells (lanes 2 and 4) as evidenced by the increased conversion of Bodipy-LPA to Bodipy-PA. Addition of lipid A to the cell extracts has little effect on LPAAT activity (lanes 2 vs 4 and 3 vs 5). A549 cell extract also contains a phosphohydrolase activity that converts Bodipy-LPA to Bodipy-monoalkylglycerol (lanes 2 to 5). Interestingly, A549 cells overexpressing LPAAT (lanes 3 and 5) have less of this activity compared to control cells (lanes 2 and 4), suggesting this phosphohydrolase prefers LPA to PA as substrate. There is also an increase of DAG in transfected cells (lanes 3 and 5) compared to control cells (lanes 2 and 4) possibly due to partial conversion of the PA formed to DAG from this endogenous phosphohydrolase.

EXAMPLE 4

To see if the expressed LPAAT cDNA clone described here would also use other glycerol-lipids that contain a free-hydroxyl group at the SN2 position, the cell extracts were incubated with the substrates NBD-lysoPC (lanes 6 and 7) and NBD-monoacylglycerol (MAG) (lanes 10 and 11) to see if there is increased conversion to lysoPC and DAG, respectively. Lane 8 and 12 refer, respectively, to NBD-lysoPC and NBD-MAG incubated with buffer only without any cell extract added. TLC analysis shows little difference in the lipid profile between the transfected and control cells (lanes 7 vs 6, lanes 11 vs 10), suggesting the cloned LPAAT enzyme uses LPA as the preferred substrate. It is likely that the acyltransferases for lysoPC (Fyrst, et al., *Biochem. J.* 306:793–799, 1995) and for MAG (Bhat, et al., *Biochemistry* 34: 11237–11244, 1995) represent different enzymes from the LPAAT described here.

EXAMPLE 5 pCE9.LPAAT 1 DNA was transfected into A549 cells (American Type Culture Collection, Rockville, Md.), a human cell line that would produce IL-6 and TNF upon stimulation with IL-1β and murine TNF. pCE9.LPAAT 1 was digested with BspH I before electroporating into A549 cells with a Cell-Porator™ (Life Technologies, Gaithersburg, Md.) using conditions described previously (Cachianes, et al., *Biotechniques* 15:255–259, 1993). After adherence of the transfected cells 24 hours later, the cells were grown in the presence of 200 μg/ml Hygromycin B (Hyg) (Calbiochem, La Jolla, Calif.) to select for cells that had incorporated both plasmids. A Hyg-resistant clone that expressed LPAAT mRNA at a level more than 20 fold higher relative to untranfected A549 cells based on Northern Blot analysis (Kroczek et al., *Anal. Biochem.* 184:90–95, 1990) was selected for further study.

Figure 7:
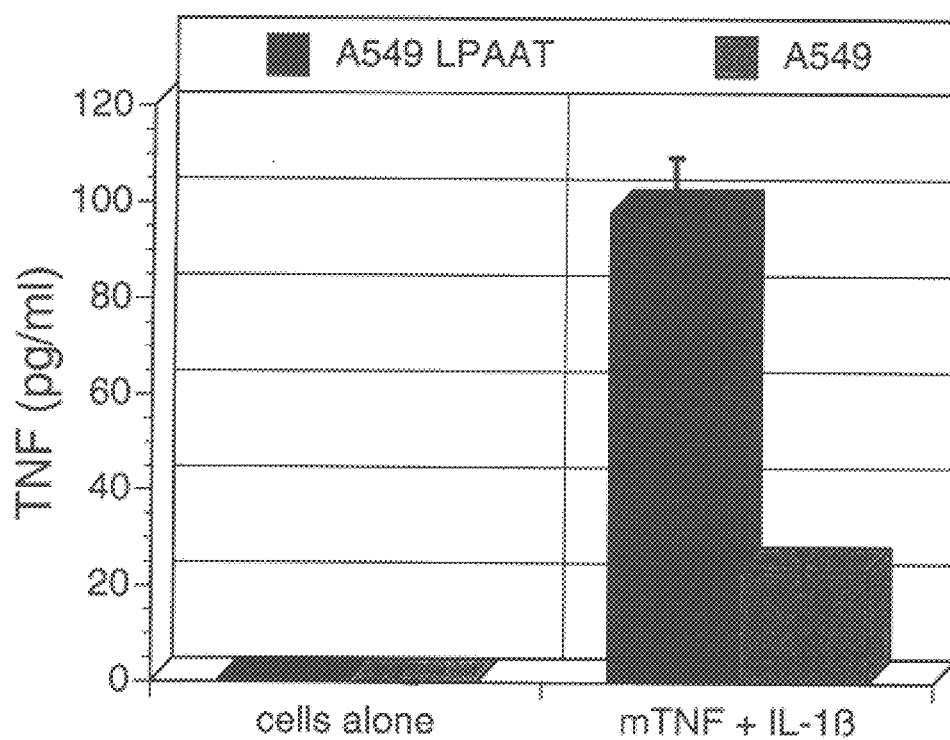
FIGS. 7 and 8 show a comparison of the production of TNF (FIG. 7) and IL-6 (FIG. 8) between A549 cells transfected with pCE9.LPAAT1 and control A549 cells after stimulation with IL-1β and murine TNF. These data show A549 overexpressing LPAAT produces >5 fold more TNF and >10 fold more IL-6 relative to untransfected A549 cells, suggesting that overexpression of LPAAT enhances the cytokine signaling response in cells.
Figure 8:
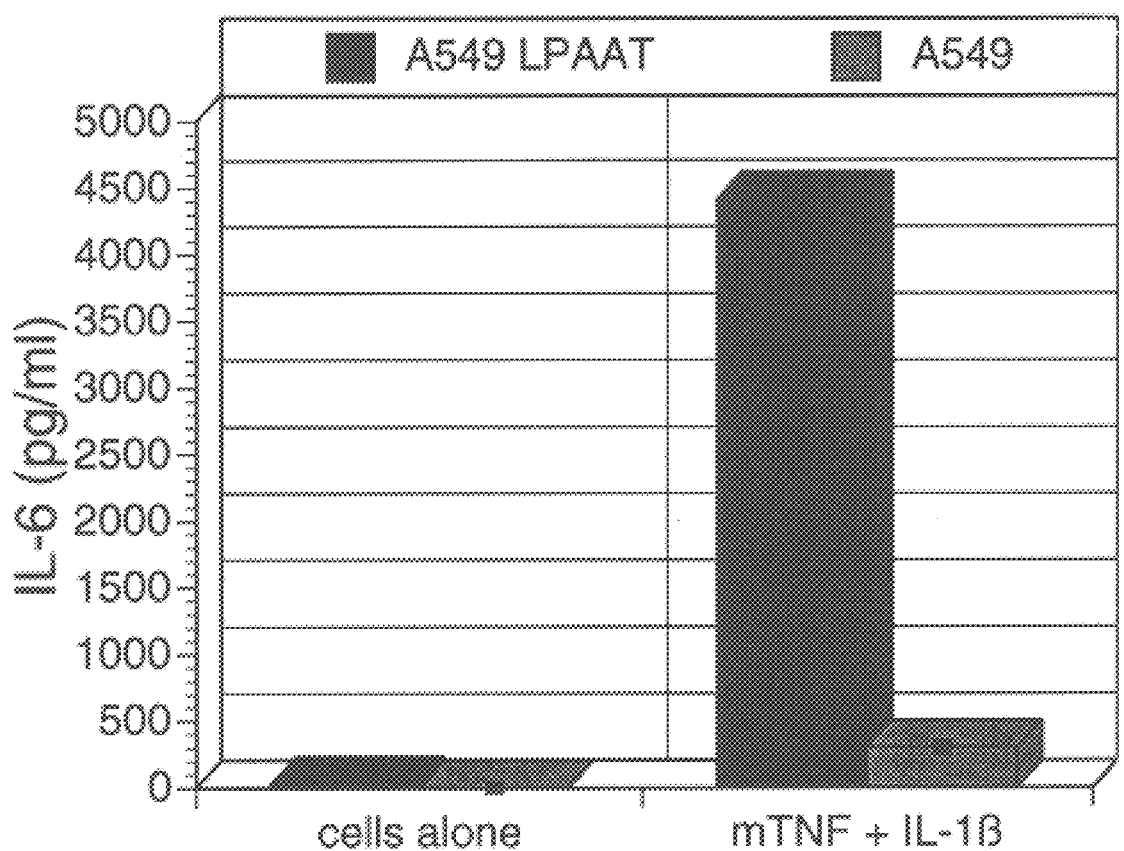

A comparison of the production of TNF (FIG. 7) and IL-6 (FIG. 8) between A549 cells transfected with pCE9.LPAAT1 and control A549 cells after stimulation with IL-1β and murine TNF shows A549 overexpressing LPAAT produces >5 fold more TNF and >10 fold more IL-6 relative to untransfected A549 cells, suggesting that overexpression of LPAAT would enhance the cytokine signaling response in cells. Development of compounds that would modulate LPAAT activity should therefore be of therapeutic interest in the field of inflammation.

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
      (A) LENGTH:2242
      (B) TYPE: nucleic acid
      (C) STRANDEDNESS: double stranded
      (D) TOPOLOGY: linear (ii) MOLECULE TYPE: cDNA to mRNA (iii) HYPOTHETICAL: no (iv) ANTI-SENSE: no (v) FRAGMENT TYPE:

(vi) ORIGINAL SOURCE:
      (A) ORGANISM: homo sapien
      (B) STRAIN:
      (C) INDIVIDUAL ISOLATE:
      (D) DEVELOPMENTAL STAGE:
      (E) HAPLOTYPE:
      (F) TISSUE TYPE: brain
      (G) CELL TYPE:
      (H) CELL LINE:
      (I) ORGANELLE:

(ix) FEATURE:
      (A) NAME/KEY: hLPAATa (xi) SEQUENCE DESCRIPTION: SEQ ID NO:1:

```
GGAAGTCAGC AGGCGTTGGG GAGGGGTGGC GGGGGAATAG CGGCGGCAGC              50

AGCCCCAGCC CTCAGAGAGA CAGCAGAAAG GGAGGGAGGG AGGGTGCTGG             100

GGGGACAGCC CCCCACCATT CCTACCGCTA TGGGCCCAAC CTCCCACTCC             150

CACCTCCCCT CCATCGGCCG GGGCTAGGAC ACCCCCAAAT CCCGTCGCCC             200

CCTTGGCACC GACACCCCGA CAGAGACAGA GACACAGCCA TCCGCCACCA             250

CCGCTGCCGC AGCCTGGCTG GGGAGGGGGC CAGCCCCCCA GGCCCCCTAC             300

CCCTCTGAGG TGGCCAGA                                               318

ATG GAT TTG                                                       327
Met Asp Leu
1

TGG CCA GGG GCA TGG ATG CTG CTG CTG CTG CTC TTC CTG CTG CTG       372
Trp Pro Gly Ala Trp Met Leu Leu Leu Leu Leu Phe Leu Leu Leu
    5                  10                  15
```

-continued

| | |
|---|---|
| CTC TTC CTG CTG CCC ACC CTG TGG TTC TGC AGC CCC AGT GCC AAG<br>Leu Phe Leu Leu Pro Thr Leu Trp Phe Cys Ser Pro Ser Ala Lys<br>20                        25                   30 | 417 |
| TAC TTC TTC AAG ATG GCC TTC TAC AAT GGC TGG ATC CTC TTC CTG<br>Tyr Phe Phe Lys Met Ala Phe Tyr Asn Gly Trp Ile Leu Phe Leu<br>35                        40                   45 | 462 |
| GCT GTG CTC GCC ATC CCT GTG TGT GCC GTG CGA GGA CGC AAC GTC<br>Ala Val Leu Ala Ile Pro Val Cys Ala Val Arg Gly Arg Asn Val<br>50                        55                   60 | 507 |
| GAG AAC ATG AAG ATC TTG CGT CTA ATG CTG CTC CAC ATC AAA TAC<br>Glu Asn Met Lys Ile Leu Arg Leu Met Leu Leu His Ile Lys Tyr<br>65                        70                   75 | 552 |
| CTG TAC GGG ATC CGA GTG GAG GTG CGA GGG GCT CAC CAC TTC CCT<br>Leu Tyr Gly Ile Arg Val Glu Val Arg Gly Ala His His Phe Pro<br>80                        85                   90 | 597 |
| CCC TCG CAG CCC TAT GTT GTT GTC TCC AAC CAC CAG AGC TCT CTC<br>Pro Ser Gln Pro Tyr Val Val Val Ser Asn His Gln Ser Ser Leu<br>95                        100                105 | 642 |
| GAT CTG CTT GGG ATG ATG GAG GTA CTG CCA GGC CGC TGT GTG CCC<br>Asp Leu Leu Gly Met Met Glu Val Leu Pro Gly Arg Cys Val Pro<br>110                    115                120 | 687 |
| ATT GCC AAG CGC GAG CTA CTG TGG GCT GGC TCT GCC GGG CTG GCC<br>Ile Ala Lys Arg Glu Leu Leu Trp Ala Gly Ser Ala Gly Leu Ala<br>125                    130                135 | 732 |
| TGC TGG CTG GCA GGA GTC ATC TTC ATC GAC CGG AAG CGC ACG GGG<br>Cys Trp Leu Ala Gly Val Ile Phe Ile Asp Arg Lys Arg Thr Gly<br>140                    145                150 | 777 |
| GAT GCC ATC AGT GTC ATG TCT GAG GTC GCC CAG ACC CTG CTC ACC<br>Asp Ala Ile Ser Val Met Ser Glu Val Ala Gln Thr Leu Leu Thr<br>155                    160                165 | 822 |
| CAG GAC GTG AGG GTC TGG GTG TTT CCT GAG GGA ACG AGA AAC CAC<br>Gln Asp Val Arg Val Trp Val Phe Pro Glu Gly Thr Arg Asn His<br>170                    175                180 | 867 |
| AAT GGC TCC ATG CTG CCC TTC AAA CGT GGC GCC TTC CAT CTT GCA<br>Asn Gly Ser Met Leu Pro Phe Lys Arg Gly Ala Phe His Leu Ala<br>185                    190                195 | 912 |
| GTG CAG GCC CAG GTT CCC ATT GTC CCC ATA GTC ATG TCC TCC TAC<br>Val Gln Ala Gln Val Pro Ile Val Pro Ile Val Met Ser Ser Tyr<br>200                    205                210 | 957 |
| CAA GAC TTC TAC TGC AAG AAG GAG CGT CGC TTC ACC TCG GGA CAA<br>Gln Asp Phe Tyr Cys Lys Lys Glu Arg Arg Phe Thr Ser Gly Gln<br>215                    220                225 | 1002 |
| TGT CAG GTG CGG GTG CTG CCC CCA GTG CCC ACG GAA GGG CTG ACA<br>Cys Gln Val Arg Val Leu Pro Pro Val Pro Thr Glu Gly Leu Thr<br>230                    235                240 | 1047 |
| CCA GAT GAC GTC CCA GCT CTG GCT GAC AGA GTC CGG CAC TCC ATG<br>Pro Asp Asp Val Pro Ala Leu Ala Asp Arg Val Arg His Ser Met<br>245                    250                255 | 1092 |
| CTC ACT GTT TTC CGG GAA ATC TCC ACT GAT GGC CGG GGT GGT GGT<br>Leu Thr Val Phe Arg Glu Ile Ser Thr Asp Gly Arg Gly Gly Gly<br>260                    265                270 | 1137 |
| GAC TAT CTG AAG AAG CCT GGG GGC GGT GGG TGA<br>Asp Tyr Leu Lys Lys Pro Gly Gly Gly Gly Stop<br>275                    280 | 1170 |
| ACCCTGGCTC TGAGCTCTCC TCCCATCTGT CCCCATCTTC CTCCCCACAC | 1220 |
| CTACCCACCC AGTGGGCCCT GAAGCAGGGC CAAACCCTCT TCCTTGTCTC | 1270 |
| CCCTCTCCCC ACTTATTCTC CTCTTTGGAA TCTTCAACTT CTGAAGTGAA | 1320 |
| TGTGGATACA GCGCCACTCC TGCCCCCTCT TGGCCCCATC CATGGACTCT | 1370 |

```
TGCCTCGGTG CAGTTTCCAC TCTTGACCCC CACCTCCTAC TGTCTTGTCT        1420

GTGGGACAGT TGCCTCCCCC TCATCTCCAG TGACTCAGCC TACACAAGGG        1470

AGGGGAACAT TCCATCCCCA GTGGAGTCTC TTCCTATGTG GTCTTCTCTA        1520

CCCCTCTACC CCCACATTGG CCAGTGGACT CATCCATTCT TTGGAACAAA        1570

TCCCCCCCCA CTCCAAAGTC CATGGATTCA ATGGACTCAT CCATTTGTGA        1620

GGAGGACTTC TCGCCCTCTG GCTGGAAGCT GATACCTGAA GCACTCCCAG        1670

GCTCATCCTG GGAGCTTTCC TCAGCACCTT CACCTTCCCT CCCAGTGTAG        1720

CCTCCTGTCA GTGGGGCTG GACCCTTCTA ATTCAGAGGT CTCATGCCTG         1770

CCCTTGCCCA GATGCCCAGG GTCGTGCACT CTCTGGGATA CCAGTTCAGT        1820

CTCCACATTT CTGGTTTTCT GTCCCCATAG TACAGTTCTT CAGTGGACAT        1870

GACCCCACCC AGCCCCCTGC AGCCCTGCTG ACCATCTCAC CAGACACAAG        1920

GGGAAGAAGC AGACATCAGG TGCTGCACTC ACTTCTGCCC CCTGGGGAGT        1970

TGGGAAAGG AACGAACCCT GGCTGGAGGG GATAGGAGGG CTTTTAATTT         2020

ATTTCTTTTT CTGTTGAGGC TTCCCCCTCT CTGAGCCAGT TTTCATTTCT        2070

TCCTGGTGGC ATTAGCCACT CCCTGCCTCT CACTCCAGAC CTGTTCCCAC        2120

AACTGGGGAG GTAGGCTGGG AGCAAAAGGA GAGGGTGGGA CCCAGTTTTG        2170

CGTGGTTGGT TTTTATTAAT TATCTGGATA ACAGCAAAAA AACTGAAAAT        2220

AAAGAGAGAG AGAAAAAAAA AA                                      2242

(2) INFORMATION FOR SEQ ID NO:2:

(i) SEQUENCE CHARACTERISTICS:
        (A) LENGTH:283
        (B) TYPE: amino acid
        (C) STRANDEDNESS: single
        (D) TOPOLOGY: linear (ii) MOLECULE TYPE: polypeptide (iii) HYPOTHETICAL: no (iv) ANTI-SENSE: NO (v) FRAGMENT TYPE:

(vi) ORIGINAL SOURCE:
        (A) ORGANISM: homo sapien
        (B) STRAIN:
        (C) INDIVIDUAL ISOLATE:
        (D) DEVELOPMENTAL STAGE:
        (E) HAPLOTYPE:
        (F) TISSUE TYPE: brain
        (G) CELL TYPE:
        (H) CELL LINE:
        (I) ORGANELLE:

(ix) FEATURE:
        (A) NAME/KEY: hLPAATa
        (B) LOCATION:
        (C) IDENTIFICATION METHOD:
        (D) OTHER INFORMATION:

(xi) SEQUENCE DESCRIPTION: SEQ ID NO:2:

Met Asp Leu Trp Pro Gly Ala Trp Met Leu
                 1               5                  10

Leu Leu Leu Leu Phe Leu Leu Leu Phe Leu Leu Pro Thr Leu
            15                  20                  25
```

```
Trp Phe Cys Ser Pro Ser Ala Lys Tyr Phe Lys Met Ala Phe
                30                  35                  40

Tyr Asn Gly Trp Ile Leu Phe Leu Ala Val Leu Ala Ile Pro Val
            45                  50                  55

Cys Ala Val Arg Gly Arg Asn Val Glu Asn Met Lys Ile Leu Arg
                60                  65                  70

Leu Met Leu Leu His Ile Lys Tyr Leu Tyr Gly Ile Arg Val Glu
                75                  80                  85

Val Arg Gly Ala His His Phe Pro Pro Ser Gln Pro Tyr Val Val
                90                  95                 100

Val Ser Asn His Gln Ser Ser Leu Asp Leu Leu Gly Met Met Glu
               105                 110                 115

Val Leu Pro Gly Arg Cys Val Pro Ile Ala Lys Arg Glu Leu Leu
               120                 125                 130

Trp Ala Gly Ser Ala Gly Leu Ala Cys Trp Leu Ala Gly Val Ile
               135                 140                 145

Phe Ile Asp Arg Lys Arg Thr Gly Asp Ala Ile Ser Val Met Ser
               150                 155                 160

Glu Val Ala Gln Thr Leu Leu Thr Gln Asp Val Arg Val Trp Val
               165                 170                 175

Phe Pro Glu Gly Thr Arg Asn His Asn Gly Ser Met Leu Pro Phe
               180                 185                 190

Lys Arg Gly Ala Phe His Leu Ala Val Gln Ala Gln Val Pro Ile
               195                 200                 205

Val Pro Ile Val Met Ser Ser Tyr Gln Asp Phe Tyr Cys Lys Lys
               210                 215                 220

Glu Arg Arg Phe Thr Ser Gly Gln Cys Gln Val Arg Val Leu Pro
               225                 230                 235

Pro Val Pro Thr Glu Gly Leu Thr Pro Asp Asp Val Pro Ala Leu
               240                 245                 250

Ala Asp Arg Val Arg His Ser Met Leu Thr Val Phe Arg Glu Ile
               255                 260                 265

Ser Thr Asp Gly Arg Gly Gly Asp Tyr Leu Lys Lys Pro Gly
               270                 275                 280

Gly Gly Gly
       283

(2) INFORMATION FOR SEQ ID NO:3:

(i) SEQUENCE CHARACTERISTICS:
        (A) LENGTH:52
        (B) TYPE: AMINO acid
        (C) STRANDEDNESS: single
        (D) TOPOLOGY: linear (ii) MOLECULE TYPE: polypeptide (iii) HYPOTHETICAL: no (iv) ANTI-SENSE: NO (v) FRAGMENT TYPE:

(vi) ORIGINAL SOURCE:
        (A) ORGANISM: yeast
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
```

```
            (H) CELL LINE:
            (I) ORGANELLE:

(ix) FEATURE:
            (A) NAME/KEY: LPAAT fragment
            (B) LOCATION:169-220
            (C) IDENTIFICATION METHOD:

(xi) SEQUENCE DESCRIPTION: SEQ ID NO:3:

Pro Phe Lys Lys Gly Ala Phe His Leu Ala Gln Gln Gly Lys Ile
 5               10                  15

Pro Ile Val Pro Val Val Ser Asn Thr Ser Thr Leu Val Ser
20              25                  30

Pro Lys Tyr Gly Val Phe Asn Arg Gly Cys Met Ile Val Arg Ile
35              40                  45

Leu Lys Pro Ile Ser Thr Glu
50       52

(2) INFORMATION FOR SEQ ID NO:4:

(i) SEQUENCE CHARACTERISTICS:
            (A) LENGTH:52
            (B) TYPE: amino acid
            (C) STRANDEDNESS: single
            (D) TOPOLOGY: linear (ii) MOLECULE TYPE: polypeptide (iii) HYPOTHETICAL: no (iv) ANTI-SENSE: no (v) FRAGMENT TYPE:

(vi) ORIGINAL SOURCE:
            (A) ORGANISM: homo sapien
            (B) STRAIN:
            (C) INDIVIDUAL ISOLATE:
            (D) DEVELOPMENTAL STAGE:
            (E) HAPLOTYPE:
            (F) TISSUE TYPE: placenta
            (G) CELL TYPE:
            (H) CELL LINE:
            (I) ORGANELLE:

(ix) FEATURE:
            (A) NAME/KEY: dbest clone #102250
            (B) LOCATION:
            (C) IDENTIFICATION METHOD:
            (D) OTHER INFORMATION:

(xi) SEQUENCE DESCRIPTION: SEQ ID NO:4:

Pro Ser Asn Cys Gly Ala Phe His Leu Ala Val Gln Ala Gln Val
              5                  10                  15

Pro Ile Val Pro Ile Val Met Ser Ser Tyr Gln Asp Phe Tyr Cys
             20                  25                  30

Lys Lys Glu Arg Arg Phe Thr Ser Gly Gln Cys Gln Val Arg Val
             35                  40

Leu Pro Pro Val Pro Thr Glu
              50       52

(2) INFORMATION FOR SEQ ID NO:5:

(i) SEQUENCE CHARACTERISTICS:
            (A) LENGTH:18
            (B) TYPE: nucleotide
            (C) STRANDEDNESS: single
            (D) TOPOLOGY: linear
```

(ii) MOLECULE TYPE: oligonucleotide fragment (iii) HYPOTHETICAL: no (iv) ANTI-SENSE: no (v) FRAGMENT TYPE:

(vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(ix) FEATURE:
            (A) NAME/KEY: o.BLPAT.2R
            (B) LOCATION:
            (C) IDENTIFICATION METHOD:
            (D) OTHER INFORMATION:

(xi) SEQUENCE DESCRIPTION: SEQ ID NO:5:

TGCAAGATGG AAGGCGCC 18

(2) INFORMATION FOR SEQ ID NO:6:

(i) SEQUENCE CHARACTERISTICS:
            (A) LENGTH:6
            (B) TYPE: amino acid
            (C) STRANDEDNESS: single
            (D) TOPOLOGY: linear (ii) MOLECULE TYPE: polypeptide fragment (iii) HYPOTHETICAL: no (iv) ANTI-SENSE: no (v) FRAGMENT TYPE:

(vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(ix) FEATURE:
            (A) NAME/KEY: o.BLPAT.2R
            (B) LOCATION:
            (C) IDENTIFICATION METHOD:
            (D) OTHER INFORMATION:

(xi) SEQUENCE DESCRIPTION: SEQ ID NO:6:

Gly Ala Phe His Leu Ala
 5       6

(2) INFORMATION FOR SEQ ID NO:7:

(i) SEQUENCE CHARACTERISTICS:
            (A) LENGTH:1383
            (B) TYPE: nucleic acid
            (C) STRANDEDNESS: double stranded
            (D) TOPOLOGY: linear (ii) MOLECULE TYPE: cDNA to mRNA (iii) HYPOTHETICAL: no (iv) ANTI-SENSE: no (v) FRAGMENT TYPE:

(vi) ORIGINAL SOURCE:
    (A) ORGANISM: homo sapien
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(ix) FEATURE:
    (A) NAME/KEY: hLPAATb (xi) SEQUENCE DESCRIPTION: SEQ ID NO:7:

```
GGAGCGAGCT GGCGGCGCCG TCGGGCGCCG GGCCGGGCC                                  39

ATG GAG CTG TGG CCG TGT CTG GCC GCG GCG CTG CTG TTG CTG CTG                 84
Met Glu Leu Trp Pro Cys Leu Ala Ala Ala Leu Leu Leu Leu Leu
1               5                   10                  15

CTG CTG GTG CAG CTG AGC CGC GCG GCC GAG TTC TAC GCC AAG GTC                129
Leu Leu Val Gln Leu Ser Arg Ala Ala Glu Phe Tyr Ala Lys Val
                20                  25                  30

GCC CTG TAC TGC GCG CTG TGC TTC ACG GTG TCC GCC GTG GCC TCG                174
Ala Leu Tyr Cys Ala Leu Cys Phe Thr Val Ser Ala Val Ala Ser
            35                  40                  45

CTC GTC TGC CTG CTG TGC CAC GGC GGC CGG ACG GTG GAG AAC ATG                219
Leu Val Cys Leu Leu Cys His Gly Gly Arg Thr Val Glu Asn Met
        50                  55                  60

AGC ATC ATC GGC TGG TTC GTG CGA AGC TTC AAG TAC TTT TAC GGG                264
Ser Ile Ile Gly Trp Phe Val Arg Ser Phe Lys Tyr Phe Tyr Gly
    65                  70                  75

CTC CGC TTC GAG GTG CGG GAC CCG CGC AGG CTG CAG GAG GCC CGT                309
Leu Arg Phe Glu Val Arg Asp Pro Arg Arg Leu Gln Glu Ala Arg
                80                  85                  90

CCC TGT GTC ATC GTC TCC AAC CAC CAG AGC ATC CTG GAC ATG ATG                354
Pro Cys Val Ile Val Ser Asn His Gln Ser Ile Leu Asp Met Met
                95                  100                 105

GGC CTC ATG GAG GTC CTT CCG GAG CGC TGC GTG CAG ATC GCC AAG                399
Gly Leu Met Glu Val Leu Pro Glu Arg Cys Val Gln Ile Ala Lys
            110                 115                 120

CGG GAG CTG CTC TTC CTG GGG CCC GTG GGC CTC ATC ATG TAC CTC                444
Arg Glu Leu Leu Phe Leu Gly Pro Val Gly Leu Ile Met Tyr Leu
        125                 130                 135

GGG GGC GTC TTC TTC ATC AAC CGG CAG CGC TCT AGC ACT GCC ATG                489
Gly Gly Val Phe Phe Ile Asn Arg Gln Arg Ser Ser Thr Ala Met
    140                 145                 150

ACA GTG ATG GCC GAC CTG GGC GAG CGC ATG GTC AGG GAG AAC CTC                534
Thr Val Met Ala Asp Leu Gly Glu Arg Met Val Arg Glu Asn Leu
                155                 160                 165

AAA GTG TGG ATC TAT CCC GAG GGT ACT CGC AAC GAC AAT GGG GAC                579
Lys Val Trp Ile Tyr Pro Glu Gly Thr Arg Asn Asp Asn Gly Asp
                170                 175                 180

CTG CTG CCT TTT AAG AAG GGC GCC TTC TAC CTG GCA GTC CAG GCA                624
Leu Leu Pro Phe Lys Lys Gly Ala Phe Tyr Leu Ala Val Gln Ala
            185                 190                 195

CAG GTG CCC ATC GTC CCC GTG GTG TAC TCT TCC TTC TCC TCC TTC                669
Gln Val Pro Ile Val Pro Val Val Tyr Ser Ser Phe Ser Ser Phe
        200                 205                 210
```

| | | |
|---|---|---|
| TAC AAC ACC AAG AAG AAG TTC TTC ACT TCA GGA ACA GTC ACA GTG<br>Tyr Asn Thr Lys Lys Lys Phe Phe Thr Ser Gly Thr Val Thr Val<br>               215                   220               225 | | 714 |
| CAG GTG CTG GAA GCC ATC CCC ACC AGC GGC CTC ACT GCG GCG GAC<br>Gln Val Leu Glu Ala Ile Pro Thr Ser Gly Leu Thr Ala Ala Asp<br>               230                   235               240 | | 759 |
| GTC CCT GCG CTC GTG GAC ACC TGC CAC CGG GCC ATG AGG ACC ACC<br>Val Pro Ala Leu Val Asp Thr Cys His Arg Ala Met Arg Thr Thr<br>               245                   250               255 | | 804 |
| TTC CTC CAC ATC TCC AAG ACC CCC CAG GAG AAC GGG GCC ACT GCG<br>Phe Leu His Ile Ser Lys Thr Pro Gln Glu Asn Gly Ala Thr Ala<br>               260                   265               270 | | 849 |
| GGG TCT GGC GTG CAG CCG GCC CAG TAG<br>Gly Ser Gly Val Gln Pro Ala Gln Stop<br>               275            278 | | 876 |
| CCCAGACCAC GGCAGGGCAT GACCTGGGGA GGGCAGGTGG AAGCCGATGG | | 926 |
| CTGGAGGATG GGCAGAGGGG ACTCCTCCCG GCTTCCAAAT ACCACTCTGT | | 976 |
| CCGGCTCCCC CAGCTCTCAC TCAGCCCGGG AAGCAGGAAG CCCCTTCTGT | | 1026 |
| CACTGGTCTC AGACACAGGC CCCTGGTGTC CCCTGCAGGG GGCTCAGCTG | | 1076 |
| GACCCTCCCC GGGCTCGAGG GCAGGGACTC GCGCCCACGG CACCTCTGGG | | 1126 |
| NGCTGGGNTG ATAAAGATGA GGCTTGCGGC TGTGGCCCGC TGGTGGGCTG | | 1176 |
| AGCCACAAGG CCCCCGATGG CCCAGGAGCA GATGGGAGGA CCCCGAGGCC | | 1226 |
| AGGAGTCCCA GACTCACGCA CCCTGGGCCA CAGGGAGCCG GGAATCGGGG | | 1276 |
| CCTGCTGCTC CTGCTGGCCT GAAGAATCTG TGGGGTCAGC ACTGTACTCC | | 1326 |
| GTTGCTGTTT TTTTATAAAC ACACTCTTGG AAAAAAAAAA AAAAAAAAA | | 1376 |
| AAAAAAA | | 1383 |

(2) INFORMATION FOR SEQ ID NO:8:

(i) SEQUENCE CHARACTERISTICS:
        (A) LENGTH:278
        (B) TYPE: amino acid
        (C) STRANDEDNESS: single
        (D) TOPOLOGY: linear (ii) MOLECULE TYPE: polypeptide (iii) HYPOTHETICAL: no (iv) ANTI-SENSE: NO (v) FRAGMENT TYPE:

(vi) ORIGINAL SOURCE:
        (A) ORGANISM: homo sapien
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(ix) FEATURE:
        (A) NAME/KEY: hLPAATb
        (B) LOCATION:
        (C) IDENTIFICATION METHOD:
        (D) OTHER INFORMATION:

(xi) SEQUENCE DESCRIPTION: SEQ ID NO:8:

```
Met Glu Leu Trp Pro Cys Leu Ala Ala Ala Leu Leu Leu Leu Leu
1               5                   10                  15

Leu Leu Val Gln Leu Ser Arg Ala Ala Glu Phe Tyr Ala Lys Val
            20                  25                  30

Ala Leu Tyr Cys Ala Leu Cys Phe Thr Val Ser Ala Val Ala Ser
            35                  40                  45

Leu Val Cys Leu Leu Cys His Gly Gly Arg Thr Val Glu Asn Met
            50                  55                  60

Ser Ile Ile Gly Trp Phe Val Arg Ser Phe Lys Tyr Phe Tyr Gly
            65                  70                  75

Leu Arg Phe Glu Val Arg Asp Pro Arg Leu Gln Glu Ala Arg
            80                  85                  90

Pro Cys Val Ile Val Ser Asn His Gln Ser Ile Leu Asp Met Met
            95                  100                 105

Gly Leu Met Glu Val Leu Pro Glu Arg Cys Val Gln Ile Ala Lys
            110                 115                 120

Arg Glu Leu Leu Phe Leu Gly Pro Val Gly Leu Ile Met Tyr Leu
            125                 130                 135

Gly Gly Val Phe Phe Ile Asn Arg Gln Arg Ser Ser Thr Ala Met
            140                 145                 150

Thr Val Met Ala Asp Leu Gly Glu Arg Met Val Arg Glu Asn Leu
            155                 160                 165

Lys Val Trp Ile Tyr Pro Glu Gly Thr Arg Asn Asp Asn Gly Asp
            170                 175                 180

Leu Leu Pro Phe Lys Lys Gly Ala Phe Tyr Leu Ala Val Gln Ala
            185                 190                 195

Gln Val Pro Ile Val Pro Val Val Tyr Ser Ser Phe Ser Ser Phe
            200                 205                 210

Tyr Asn Thr Lys Lys Lys Phe Phe Thr Ser Gly Thr Val Thr Val
            215                 220                 225

Gln Val Leu Glu Ala Ile Pro Thr Ser Gly Leu Thr Ala Ala Asp
            230                 235                 240

Val Pro Ala Leu Val Asp Thr Cys His Arg Ala Met Arg Thr Thr
            245                 250                 255

Phe Leu His Ile Ser Lys Thr Pro Gln Glu Asn Gly Ala Thr Ala
            260                 265                 270

Gly Ser Gly Val Gln Pro Ala Gln
            275         278

(2) INFORMATION FOR SEQ ID NO:9:

(i) SEQUENCE CHARACTERISTICS:
        (A) LENGTH:60
        (B) TYPE: amino acid
        (C) STRANDEDNESS: single
        (D) TOPOLOGY: linear (ii) MOLECULE TYPE: polypeptide (iii) HYPOTHETICAL: no (iv) ANTI-SENSE: NO (v) FRAGMENT TYPE:

(vi) ORIGINAL SOURCE:
        (A) ORGANISM: yeast
        (B) STRAIN:
        (C) INDIVIDUAL ISOLATE:
        (D) DEVELOPMENTAL STAGE:
```

```
            (E) HAPLOTYPE:
            (F) TISSUE TYPE:
            (G) CELL TYPE:
            (H) CELL LINE:
            (I) ORGANELLE:

(ix) FEATURE:
            (A) NAME/KEY: LPAAT fragment
            (B) LOCATION:171-230
            (C) IDENTIFICATION METHOD:

(xi) SEQUENCE DESCRIPTION: SEQ ID NO:9:

Gln Gln Gly Lys Ile Pro Ile Val Pro Val Val Ser Asn Thr
              5                  10                  15

Ser Thr Leu Val Ser Pro Lys Tyr Gly Val Phe Asn Arg Gly Cys
             20                  15                  30

Met Ile Val Arg Ile Leu Lys Pro Ile Ser Thr Glu Asn Leu Thr
             35                  40                  45

Lys Asp Lys Ile Gly Glu Phe Ala Glu Lys Val Arg Asp Gln Met
             50                  55                  60

(2) INFORMATION FOR SEQ ID NO:10:

(i) SEQUENCE CHARACTERISTICS:
            (A) LENGTH:60
            (B) TYPE: amino acid
            (C) STRANDEDNESS: single
            (D) TOPOLOGY: linear (ii) MOLECULE TYPE: polypeptide (iii) HYPOTHETICAL: no (iv) ANTI-SENSE: no (v) FRAGMENT TYPE:

(vi) ORIGINAL SOURCE:
            (A) ORGANISM: homo sapien
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(ix) FEATURE:
            (A) NAME/KEY: dbest clone #363498
            (B) LOCATION:
            (C) IDENTIFICATION METHOD:
            (D) OTHER INFORMATION:

(xi) SEQUENCE DESCRIPTION: SEQ ID NO:10:

Val Arg Glu Asn Val Pro Ile Val Pro Val Val Tyr Ser Ser Phe
              5                  10                  15

Ser Ser Phe Tyr Asn Thr Lys Lys Lys Phe Phe Thr Ser Gly Thr
             20                  25                  30

Val Thr Val Gln Val Leu Glu Ala Ile Pro Thr Ser Gly Leu Thr
             35                  40                  45

Ala Ala Asp Val Pro Ala Leu Arg Gly Thr Pro Ala Thr Gly Pro
             50                  55                  60

(2) INFORMATION FOR SEQ ID NO:11:

(i) SEQUENCE CHARACTERISTICS:
            (A) LENGTH:20
            (B) TYPE: nucleotide
```

(C) STRANDEDNESS: single
            (D) TOPOLOGY: linear (ii) MOLECULE TYPE: oligonucleotide fragment (iii) HYPOTHETICAL: no (iv) ANTI-SENSE: no (v) FRAGMENT TYPE:

(vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(ix) FEATURE:
            (A) NAME/KEY: o. LPAT.3F
            (B) LOCATION:
            (C) IDENTIFICATION METHOD:
            (D) OTHER INFORMATION:

(xi) SEQUENCE DESCRIPTION: SEQ ID NO:11:

CCTCAAAGTG TGGATCTATC                                                      20

(2) INFORMATION FOR SEQ ID NO:12:

(i) SEQUENCE CHARACTERISTICS:
            (A) LENGTH:21
            (B) TYPE: nucleotide
            (C) STRANDEDNESS: single
            (D) TOPOLOGY: linear (ii) MOLECULE TYPE: oligonucleotide (iii) HYPOTHETICAL: no (iv) ANTI-SENSE: no (v) FRAGMENT TYPE:

(vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(ix) FEATURE:
            (A) NAME/KEY: o.LPAT3.R
            (B) LOCATION:
            (C) IDENTIFICATION METHOD:
            (D) OTHER INFORMATION:

(xi) SEQUENCE DESCRIPTION: SEQ ID NO:12:

GGAAGAGTAC ACCACGGGGA C                                                    21

(2) INFORMATION FOR SEQ ID NO:13:

(i) SEQUENCE CHARACTERISTICS:
            (A) LENGTH:21
            (B) TYPE: nucleotide
            (C) STRANDEDNESS: single
            (D) TOPOLOGY: linear -continued (ii) MOLECULE TYPE: oligonucleotide (iii) HYPOTHETICAL: no (iv) ANTI-SENSE: no (v) FRAGMENT TYPE:

(vi) ORIGINAL SOURCE:
             (A) ORGANISM:
             (B) STRAIN:
             (C) INDIVIDUAL ISOLATE:
             (D) DEVELOPMENTAL STAGE:
             (E) HAPLOTYPE:
             (F) TISSUE TYPE:
             (G) CELL TYPE:
             (H) CELL LINE:
             (I) ORGANELLE:

(ix) FEATURE:
             (A) NAME/KEY: o.sport.1
             (B) LOCATION:
             (C) IDENTIFICATION METHOD:
             (D) OTHER INFORMATION:

(xi) SEQUENCE DESCRIPTION: SEQ ID NO:13:

GACTCTAGCC TAGGCTTTTG C                                              21

(2) INFORMATION FOR SEQ ID NO:14:

(i) SEQUENCE CHARACTERISTICS:
             (A) LENGTH:21
             (B) TYPE: nucleotide
             (C) STRANDEDNESS: single
             (D) TOPOLOGY: linear (ii) MOLECULE TYPE: oligonucleotide (iii) HYPOTHETICAL: no (iv) ANTI-SENSE: no (v) FRAGMENT TYPE:

(vi) ORIGINAL SOURCE:
             (A) ORGANISM:
             (B) STRAIN:
             (C) INDIVIDUAL ISOLATE:
             (D) DEVELOPMENTAL STAGE:
             (E) HAPLOTYPE:
             (F) TISSUE TYPE:
             (G) CELL TYPE:
             (H) CELL LINE:
             (I) ORGANELLE:

(ix) FEATURE:
             (A) NAME/KEY: o.sport.1R
             (B) LOCATION:
             (C) IDENTIFICATION METHOD:
             (D) OTHER INFORMATION:

(xi) SEQUENCE DESCRIPTION: SEQ ID NO:14:

CTAGCTTATA ATACGACTCA C                                              21

(2) INFORMATION FOR SEQ ID NO:15:

(i) SEQUENCE CHARACTERISTICS:
             (A) LENGTH:29
             (B) TYPE: nucleotide
             (C) STRANDEDNESS: single
             (D) TOPOLOGY: linear (ii) MOLECULE TYPE: oligonucleotide (iii) HYPOTHETICAL: no (iv) ANTI-SENSE: no (v) FRAGMENT TYPE:

(vi) ORIGINAL SOURCE:
             (A) ORGANISM:
             (B) STRAIN:
             (C) INDIVIDUAL ISOLATE:
             (D) DEVELOPMENTAL STAGE:
             (E) HAPLOTYPE:
             (F) TISSUE TYPE:
             (G) CELL TYPE:
             (H) CELL LINE:
             (I) ORGANELLE:

(ix) FEATURE:
             (A) NAME/KEY:
             (B) LOCATION:
             (C) IDENTIFICATION METHOD:
             (D) OTHER INFORMATION:

(xi) SEQUENCE DESCRIPTION: SEQ ID NO:15:

GGCTCTAGAT ATTAATAGTA ATCAATTAC                                             29

(2) INFORMATION FOR SEQ ID NO:16:

(i) SEQUENCE CHARACTERISTICS:
            (A) LENGTH:26
            (B) TYPE: nucleotide
            (C) STRANDEDNESS: single
            (D) TOPOLOGY: linear (ii) MOLECULE TYPE: oligonucleotide (iii) HYPOTHETICAL: no (iv) ANTI-SENSE: no (v) FRAGMENT TYPE:

(vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(ix) FEATURE:
            (A) NAME/KEY:
            (B) LOCATION:
            (C) IDENTIFICATION METHOD:
            (D) OTHER INFORMATION:

(xi) SEQUENCE DESCRIPTION: SEQ ID NO:16:

CCTCACGCAT GCACCATGGT AATAGC                                                26

(2) INFORMATION FOR SEQ ID NO:17:

(i) SEQUENCE CHARACTERISTICS:
            (A) LENGTH:24
            (B) TYPE: nucleotide
            (C) STRANDEDNESS: single
            (D) TOPOLOGY: linear (ii) MOLECULE TYPE: oligonucleotide (iii) HYPOTHETICAL: no (iv) ANTI-SENSE: no -continued

```
    (v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO:17:

GGTGCATGCG TGAGGCTCCG GTGC                                          24

(2) INFORMATION FOR SEQ ID NO:18:

(i) SEQUENCE CHARACTERISTICS:
        (A) LENGTH:28
        (B) TYPE: nucleotide
        (C) STRANDEDNESS: single
        (D) TOPOLOGY: linear (ii) MOLECULE TYPE: oligonucleotide (iii) HYPOTHETICAL: no (iv) ANTI-SENSE: no (v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO:18:

GTAGTTTTCA CGGTACCTGA AATGGAAG                                      28
```

We claim:

1. A nucleic acid sequence encoding a Lysophosphatidic Acid Acyltransferase (LPAAT) enzyme selected from the group consisting of:

(a) a nucleotide sequence set forth in SEQ ID NO: 1, SEQ ID NO: 7 or (b) a nucleotide sequence encoding a polypeptide of SEQ ID NO: 2, SEQ ID NO: 8 or enzymatically active fragments thereof.

2. A nucleic acid sequence which hybridizes under high stringency conditions to the nucleotide sequence of SEQ ID NO: 1 or SEQ ID NO: 7, wherein said high stringency conditions are characterized by an ionic strength equivalent to from 4× to 6× SSC, and a temperature in the range of 65° C. to 70° C. in the absence of formamide and in the range of 40° C. to 45° C. in the presence of 50% formamide.

3. A nucleic acid sequence which hybridizes under high stringency conditions to the nucleotide sequence encoding the polypeptide of SEQ ID NO: 2 or SEQ ID NO: 8, wherein said high stringency conditions are characterized by an ionic strength equivalent to from 4× to 6× SSC, and a temperature in the range of 65° C. to 70° C. in the absence of formamide and in the range of 40° C. to 45° C. in the presence of 50% formamide.

* * * * *